US010528833B1

(12) United States Patent
Bhatnagar

(10) Patent No.: US 10,528,833 B1
(45) Date of Patent: Jan. 7, 2020

(54) HEALTH MONITORING SYSTEM OPERABLE IN A VEHICLE ENVIRONMENT

(71) Applicant: Denso International America, Inc., Southfield, MI (US)

(72) Inventor: Shalabh Bhatnagar, Farmington Hills, MI (US)

(73) Assignee: Denso International America, Inc., Southfield, MI (US)

(*) Notice: Subject to any disclaimer, the term of this patent is extended or adjusted under 35 U.S.C. 154(b) by 0 days.

(21) Appl. No.: 16/055,893

(22) Filed: Aug. 6, 2018

(51) Int. Cl.
*G08B 21/08* (2006.01)
*G06K 9/00* (2006.01)
(Continued)

(52) U.S. Cl.
CPC ......... *G06K 9/00845* (2013.01); *A61B 5/024* (2013.01); *B60K 28/06* (2013.01);
(Continued)

(58) Field of Classification Search
CPC .............. B60K 37/06; B60K 2370/126; B60K 2370/143; B60K 2370/145; B60K 35/00; B60K 2370/1438; B60K 2370/146; B60K 2370/148; B60K 2370/1868; B60K 2370/21; B60K 2370/55; B60K 2370/589; B60K 2370/774; B60K 2370/785; B60K 37/02; G06F 3/0482; G06F 3/0488; G06F 16/27; G06F 19/00; G06F 19/3475; G06F 1/3209; G06F 1/3215; G06F 1/3287; G06F 21/6245; G06F 2203/04108; G06F 2203/04809; G06F 3/0312; G06F 3/03545;
(Continued)

(56) References Cited

U.S. PATENT DOCUMENTS 4,819,860 A 4/1989 Hargrove et al.
6,904,313 B1* 6/2005 Snell ................... A61B 5/0031
600/509

(Continued)

FOREIGN PATENT DOCUMENTS

CN 204423616 6/2015

OTHER PUBLICATIONS

Tanantong et al., False Alarm Reduction in BSN-Based Cardiac Monitoring Using Signal Quality and Activity Type Information (Feb. 9, 2015).

(Continued)

*Primary Examiner* — Daniel Previl
(74) *Attorney, Agent, or Firm* — Christopher G. Darrow; Darrow Mustafa PC

(57) ABSTRACT

A method of controlling a vehicle is provided. The method may include steps of: acquiring occupant pulse rate information and occupant motion information for an occupant of the vehicle; classifying, using the occupant motion information, a current activity level of the occupant into one of a plurality of predetermined activity levels; determining a range of safe pulse rates for the occupant at the current activity level; determining, using the range of safe pulse rates for the occupant, if a current pulse rate of the occupant indicates a cardiac health risk to the occupant; and, responsive to a determination that the current pulse rate of the occupant indicates a cardiac health risk to the occupant, controlling the vehicle.

19 Claims, 10 Drawing Sheets

(51) Int. Cl.
*B60W 40/08* (2012.01)
*G05D 1/00* (2006.01)
*B60K 28/06* (2006.01)
*A61B 5/024* (2006.01)

(52) U.S. Cl.
CPC .......... *B60W 40/08* (2013.01); *G05D 1/0061* (2013.01); *G05D 1/0088* (2013.01); *B60W 2040/0818* (2013.01); *B60W 2040/0872* (2013.01); *G05D 2201/0213* (2013.01)

(58) Field of Classification Search
CPC .... G06F 3/0425; G06F 3/04847; G06F 16/00; G06F 16/22; G06F 16/24575; G06F 16/29; G06F 16/436; G06F 16/444; G06F 16/9535; G06F 19/3481; G06F 21/32; G06F 2203/011; G06F 3/011; G06F 3/017; G06F 3/0421; G06F 3/04883; G06F 3/04886; G06F 3/165; G06F 3/167; G16H 10/60; G16H 50/20; G16H 40/63; G16H 50/30; H04L 67/306; H04L 63/0428; H04L 63/0861; H04L 67/025; H04L 67/04; H04L 67/10; H04L 67/12; H04L 67/22; H04L 67/32; H04L 67/18; G01C 21/3664; G01C 21/265; G01C 21/365; G06Q 10/1097; G06Q 40/08; G06Q 50/12; G06Q 50/22; B60H 1/00642; B60H 1/00657; B60H 1/00742; B60R 16/02; B60R 16/037; H04W 4/046; H04W 4/38; H04W 4/50; A61B 5/01; A61B 5/02438; A61B 5/11; A61B 5/14507; A61B 5/14546; A61M 2021/0022; A61M 21/00; A61M 2205/3553; A61M 2210/0625; A61M 2230/005; A61M 2230/06; A63B 24/0062; A63B 24/0075; B60J 1/02; B60Y 2400/92; G06N 20/00; G06N 5/048; G06N 7/005; G09B 19/00; G09B 5/125; H04R 1/1016; H04R 1/1041; H04R 1/1091; H04R 2227/005; H04R 2420/07; H04R 2430/01; H04R 2499/13

USPC ...... 340/573.6, 436, 425.5, 500, 540, 573.1, 340/576, 435
See application file for complete search history.

(56) References Cited

U.S. PATENT DOCUMENTS

| | | | |
|---|---|---|---|
| 7,139,607 B1* | 11/2006 | Shelchuk | A61N 1/3622 607/9 |
| 7,539,533 B2 | 5/2009 | Tran | |
| 9,171,445 B2 | 10/2015 | Nishihara et al. | |
| 9,572,503 B2 | 2/2017 | DeForest | |
| 9,759,570 B2 | 9/2017 | Joao et al. | |
| 9,897,459 B2 | 2/2018 | Johnson | |
| 2003/0176798 A1 | 9/2003 | Simon | |
| 2008/0266118 A1 | 10/2008 | Pierson et al. | |
| 2008/0294058 A1* | 11/2008 | Shklarski | A61B 5/02055 600/502 |
| 2011/0066007 A1* | 3/2011 | Banet | A61B 5/0402 600/301 |
| 2015/0351695 A1 | 12/2015 | Cronin | |
| 2015/0351698 A1* | 12/2015 | Cronin | A61B 5/0022 600/485 |
| 2016/0338642 A1 | 11/2016 | Parara et al. | |
| 2017/0173262 A1* | 6/2017 | Veltz | A61M 5/1723 |
| 2017/0209055 A1* | 7/2017 | Pantelopoulos | A61B 5/02438 |
| 2017/0258329 A1 | 9/2017 | Marsh | |
| 2018/0059621 A1 | 3/2018 | Singh | |
| 2018/0078219 A1 | 3/2018 | Selvaraj | |

OTHER PUBLICATIONS

Ryan et al., Relations between Alcohol Consumption, Heart Rate, and Heart Rate Variability in Men (Dec. 2002).

Kakria et al.,A Real-Time Health Monitoring System for Remote Cardiac Patients Using Smartphone and Wearable Sensors (Nov. 12, 2015).

Fidler et al. Understanding Heart Rate Alarm Adjustment in the Intensive Care Units through an Analytical Approach (Nov. 27, 2017).

Bhatnagar, Integration of V2V-AEB System with Wearable Cardiac Monitoring System and Reduction of V2V-AEB System Time Constraints (Aug. 2017).

* cited by examiner

Table of Average Heart Rates

| Newborns | 1-30 days old | 70-190 |
|---|---|---|
| Infants | 1-11 months | 80-160 |
| Toddlers | 1-2 years old | 80-130 |
| Preschoolers | 3-4 years old | 80-120 |
| Elementary Age | 5-10 years | 70-115 |
| Teenagers | 10-20 years | 60-100 |
| Adults | 20-60 years | 60-100 |

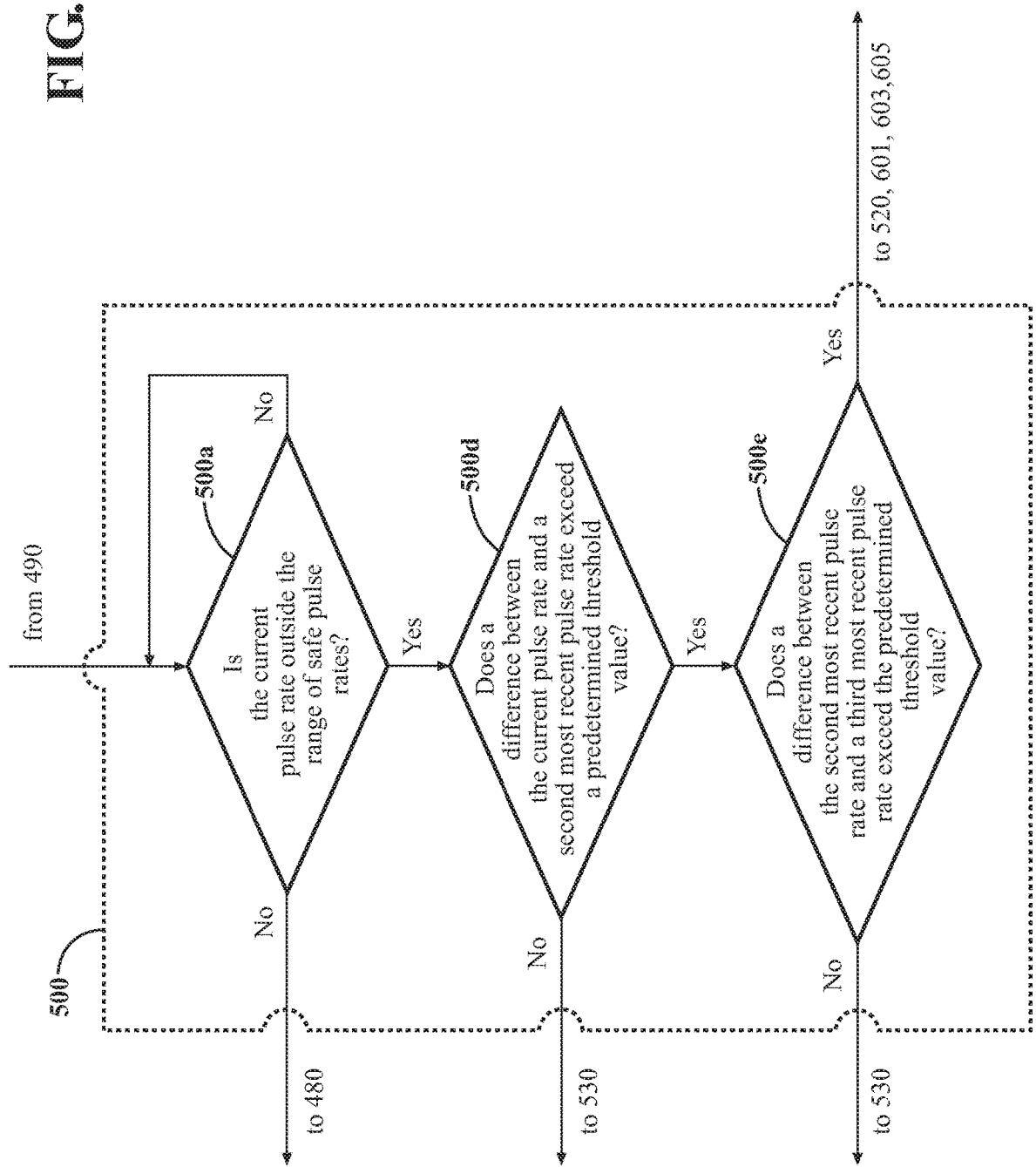

US 10,528,833 B1

HEALTH MONITORING SYSTEM OPERABLE IN A VEHICLE ENVIRONMENT

TECHNICAL FIELD

The present disclosure relates to health monitoring systems and, more particularly, to a health monitoring system usable in a vehicle to monitor a pulse rate of a vehicle occupant.

BACKGROUND

Autonomous and semi-autonomous vehicles may be configured for self-driving without input from human operators in many driving situations. However, in various situations, a human driver may need to exercise a degree of manual vehicle control. Many drivers may also have chronic or unknown health conditions, such as cardiac conditions, which may affect the driver at any time, including while driving. If these health conditions in the driver manifest and/or worsen suddenly while the driver is operating the vehicle, a dangerous condition result for the driver, other occupants of the vehicle, and other vehicles in the immediate vicinity.

SUMMARY OF THE INVENTION

In one aspect of the embodiments described herein, a method of controlling a vehicle is provided. The method may include steps of: acquiring occupant pulse rate information and occupant motion information for an occupant of the vehicle; classifying, using the occupant motion information, a current activity level of the occupant into one of a plurality of predetermined activity levels; determining a range of safe pulse rates for the occupant at the current activity level; determining, using the range of safe pulse rates for the occupant, if a current pulse rate of the occupant indicates a cardiac health risk to the occupant; and, responsive to a determination that the current pulse rate of the occupant indicates a cardiac health risk to the occupant, controlling the vehicle.

In another aspect of the embodiments described herein, a system for autonomously controlling a vehicle is provided. The system for autonomously controlling the vehicle may include a vehicle computing system and a health monitoring system. The health monitoring system may include one or more health monitoring system processors, and a health monitoring system memory in communication with the one or more health monitoring system processors. The health monitoring system memory may be configured for storing information and program instructions usable by the one or more health monitoring system processors, and may store a user activity level classification module including instructions that when executed by the one or more processors cause the one or more processors to classify a current activity level of a vehicle occupant using motion information relating to the occupant. The health monitoring system memory may also store a cardiac health risk determination module including instructions that when executed by the one or more health monitoring system processors cause the one or more processors to determine if a current pulse rate of the vehicle occupant at the current activity level indicates a cardiac health risk to the vehicle occupant. The health monitoring system memory may also store a health alert generation module including instructions that when executed by the one or more processors cause the one or more processors to, responsive to a determination that a current pulse rate of the vehicle occupant indicates a cardiac health risk to the vehicle occupant, generate one or more health alert signals to the vehicle computing system. The vehicle computing system may be in communication with the health monitoring system and may be configured for autonomously controlling the vehicle. The vehicle computing system may include one or more processors for controlling operation of the vehicle computing system, and a memory for storing data and program instructions usable by the one or more processors for controlling operation of the vehicle computing system. The one or more processors for controlling operation of the vehicle computing system may be configured to execute instructions stored in the memory to control the vehicle responsive to receipt of the health alert signal from the health monitoring system.

BRIEF DESCRIPTION OF THE DRAWINGS

The accompanying drawings, which are incorporated in and constitute a part of this specification, illustrate embodiments described herein and together with the description serve to explain principles of embodiments described herein.

FIG. 5 is a flow diagram showing, in greater detail, an embodiment of one of the operational steps shown in FIG. 3.

DETAILED DESCRIPTION

Embodiments described herein relate to a health monitoring system configured to continuously measure a pulse rate of a user, and to determine when the user pulse rate reaches a level indicating a cardiac health risk to the user. When a cardiac health risk is determined, the health monitoring system may trigger one or more health alerts to entities such as emergency services facilities and family and friends of the user. In one or more particular applications, the health monitoring system may be configured to operate in a vehicle environment with the user as an occupant of the vehicle. The vehicle may be configured for autonomous or semi-autonomous operation. Various operational aspects of the vehicle may be controlled by a vehicle computing system. The health monitoring system may be configured to operate in conjunction with the vehicle computing system to provide a vehicle control system configured for controlling aspects of vehicle operation responsive to detection of a pulse rate determined to indicate a cardiac health risk to the user. For example, the vehicle may be controlled to pull the vehicle over to a side of a road, or to drive the vehicle to a predetermined location. Health alert signals may also be generated to surrounding vehicles. Also, various audible and/or visual alert indicators of the health alert may be activated, such as the vehicle exterior lights or horn.

For purposes described herein, the "pulse rate" is the measured number of pulsations or pulses in an artery per unit of time. The pulse rate is normally the same as the heart rate. For purposes described herein, the unit of time may be one minute (i.e., the pulse rate is calculated using the number of pulses measured over a period of one minute), although other pulse measurement time frames may be used for specific purposes. A pulse may be detected graphically as a peak in a graph or chart of the measured pulse rate, or the peak(s) defining the pulses may be determined in a known manner from sensor data, for example.

Figure 1:
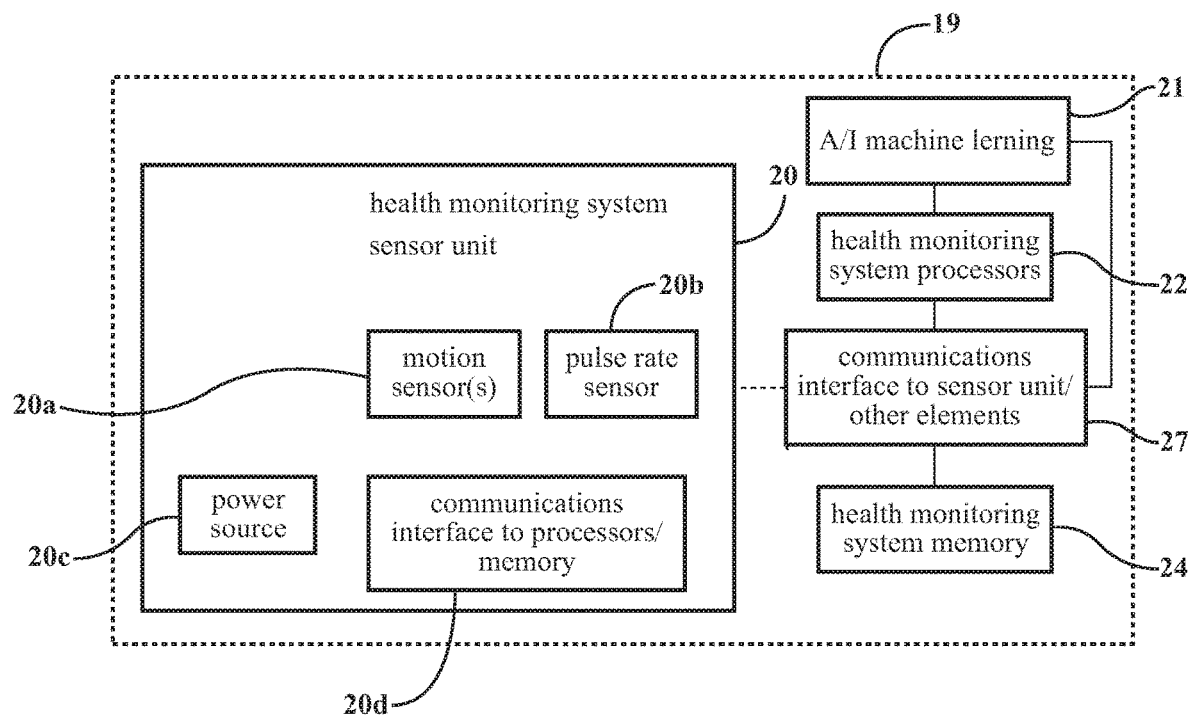
FIG. 1 is a schematic block diagram of a health monitoring system in accordance with an embodiment described herein.

FIG. 1 is a schematic block diagram of a health monitoring system 19 in accordance with an embodiment described herein. In the embodiment shown, the health monitoring system 19 may include one or more motion sensors 20a, a pulse rate sensor 20b, one or more health monitoring system processors 22, and a health monitoring system memory 24. The health monitoring system 19 may also include one or more communications interfaces (such as interfaces 20d and 27) enabling communications between elements of the health monitoring system 19 and also between the health monitoring system 19 and other systems or entities.

The pulse rate sensor 20b may be configured to measure a pulse rate of a user to which the sensor is attached or connected. Any of a variety of known pulse rate sensors may be employed for the purposes described herein. In a particular embodiment, the pulse rate sensor may have a sampling rate of 9 Hz.

The pulse rate sensor 20b may also be configured to acquire other data in addition to pulse rate. Also, various characteristics of the pulse rate may be extracted or derived from the measured pulse rate and/or by the pulse rate sensor 20b. For example, a pulse rise rate (an average rate at which the pulse rises to the peak, or the slope of the portion of a pulse rate graph immediately preceding the peak) may derived from a graph or otherwise determined from pulse rate sensor data. Also, a pulse fall rate (an average rate at which the pulse falls from the peak, or the slope of the portion of a pulse rate graph immediately following the peak) may derived from a graph or otherwise determined from pulse rate sensor data. The values of these parameters may be used (in conjunction with user personal information and other information) by machine learning algorithms to help tailor values of individual analysis parameters to a particular user, which improves the overall accuracy and effectiveness of the health monitoring system.

In one or more embodiments described herein, a physical activity level of a user is measured using data from motion sensor(s) 20a reflecting the acceleration of a portion of a body of the user when the portion of the body is moving. In one or more arrangements, the motion sensor(s) 20a may be in the form of an inertial measurement unit (IMU), accelerometer, or other sensor device configured to measure x, y, and z acceleration components $a_x$, $a_y$, $a_z$ of motion of a user to which the motion sensor is attached. In a particular embodiment, the accelerometer may have a sampling rate of 100 Hz.

Although embodiments of the health monitoring system described herein may use any of various types of acceleration sensing devices to detect and quantify motion of the user, it is understood that other parameters may be used to detect and estimate the magnitude, speed, and/or direction of the user's motion and to quantify these parameters for use by the health monitoring system, provided that these parameters correlate with the user's pulse rate (i.e., the changes in the motion parameters used should relate to, and be time-correlatable with, changes in the user's pulse rate).

The acceleration sensor(s) 20a and the pulse rate sensor 20b may be configured for wired or wireless connection to another device or to a portion of a vehicle. Referring to FIG. 1, in one or more arrangements, the acceleration and pulse rate sensor(s) 20a, 20b may be incorporated into a health monitoring system sensor unit, generally designated 20. In one or more examples, the health monitoring system sensor unit 20 may be a wearable device, such as a wrist-mounted device. The health monitoring system sensor unit 20 including the acceleration sensor(s) 20a and the pulse rate sensor 20b may also incorporate a communications interface 20d configured to wirelessly (or by wire) communicate pulse rate and acceleration information to one or more health monitoring system processors 22 and/or to other elements or systems. The health monitoring system sensor unit 20 may also incorporate a power source 20c for powering elements of the sensor unit 20.

Figure 7:
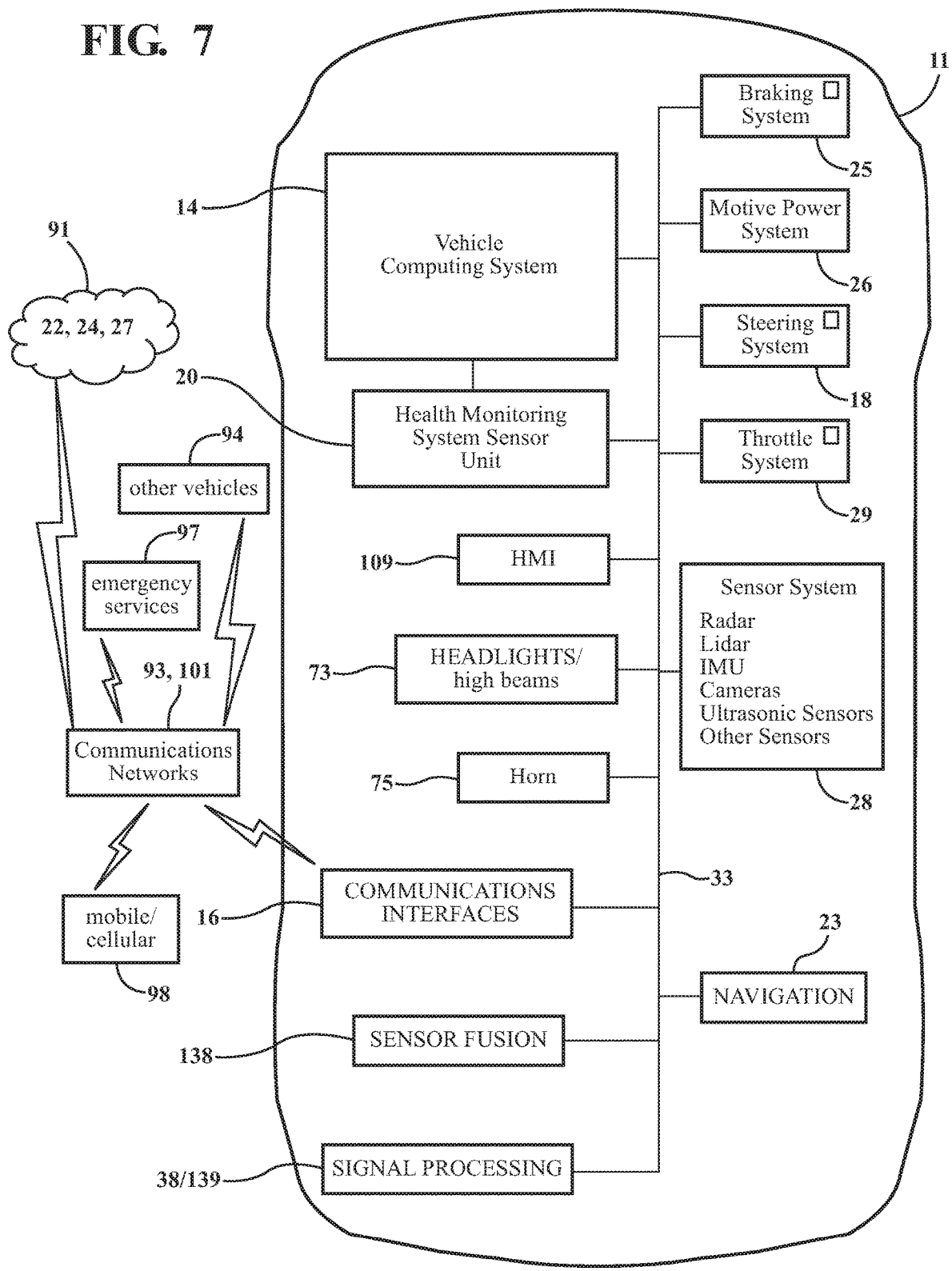
FIG. 7 is a schematic block diagram of a health monitoring system/vehicle configuration, including a vehicle and an embodiment of a health monitoring system configured for operating in the vehicle.
Figure 8:
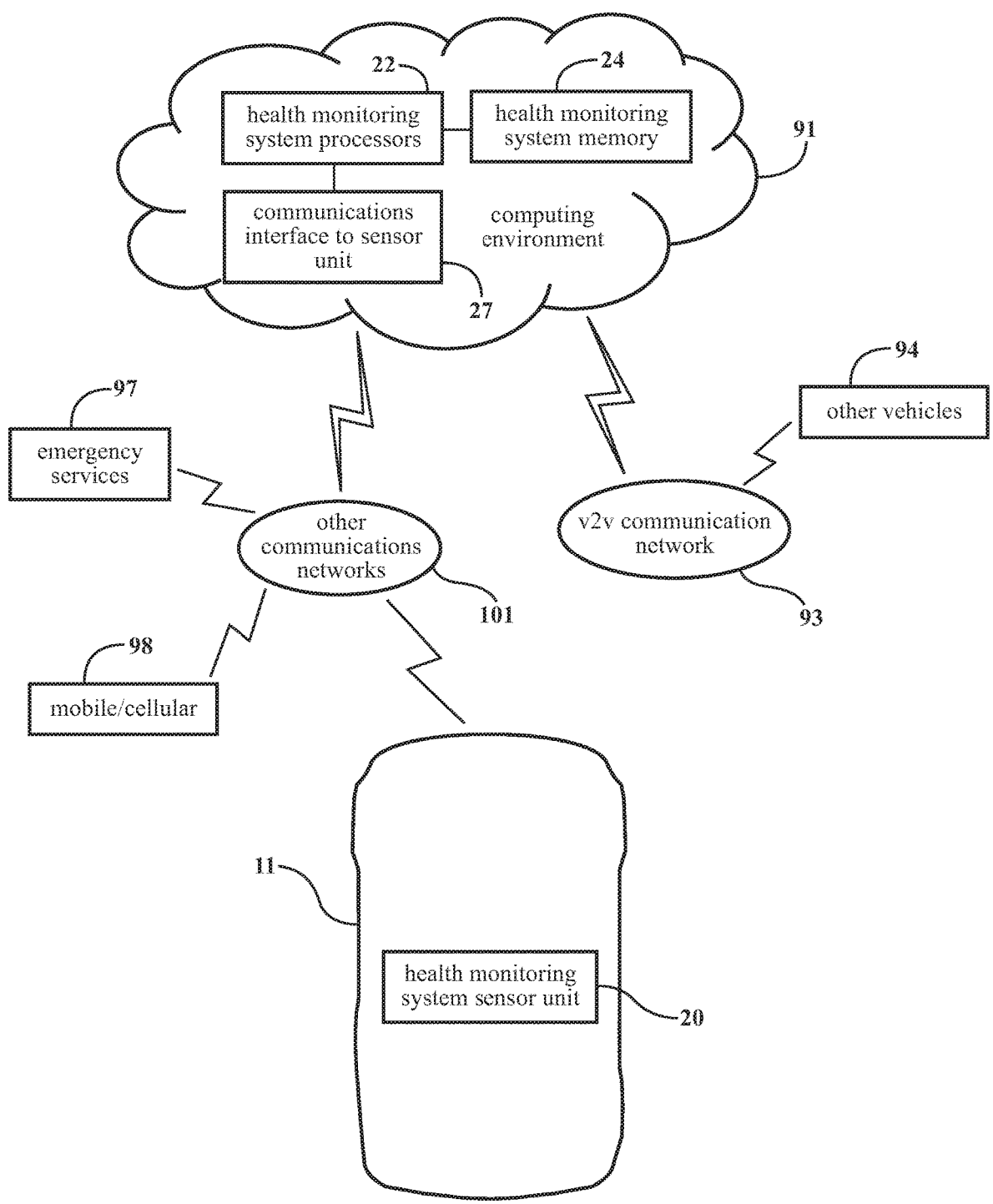
FIG. 8 is a schematic block diagram showing one embodiment of a distributed structure of a health monitoring system, operating in the vehicle environment shown in FIG. 7.

The health monitoring system sensor unit communications interface 20d may be communicatively coupled to the sensors 20a, 20b to enable communication between health monitoring system sensor unit 20 and other elements of the health monitoring system 19. In arrangements where the elements of the health monitoring system 19 are distributed among various units or entities (such as shown in FIGS. 7 and 8, described in greater detail below), one or more additional communications interfaces (such as communications interface 27) may be coupled to processors 22 and memory 24 to enable communication between the sensors 20a, 20b (via communications interface 20d) and the processors 22 and memory 24, thereby enabling the processing functions to be performed remotely from the sensors. For example, health monitoring system processors 22 and memory 24 may be located in a cloud computing environment (discussed in more detail below in connection with FIGS. 7 and 8) or in another computing environment remote from the user. In such arrangements, the communications interfaces 20d and 27 may enable wireless communications between various separate elements of the health monitoring system. Also, as discussed in greater detail below, the communications interface 27 may also enable communication between the health monitoring system and other vehicles (via a vehicle-to-vehicle (V2V) communications network), cellular devices, emergency services, and other entities.

Referring again to FIG. 1, the health monitoring system 19 may include one or more health monitoring system processors 22 configured for processing user pulse rate and acceleration data as described herein. As used herein, "processor" means any component or group of components that are configured to execute any of the processes and/or process steps described herein, or any form of instructions needed to carry out such processes/process steps or cause such processes/process steps to be performed. The processor (s) described herein may be implemented with one or more general-purpose and/or one or more special-purpose processors. Examples of suitable processors include microprocessors, controllers, microcontrollers, DSP processors, and other circuitry that can execute software. The processor(s) can include at least one hardware circuit (e.g., an integrated circuit) configured to carry out instructions contained in program code. In arrangements in which there is a plurality of processors, such processors can work independently from each other or one or more processors can work in combination with each other.

The health monitoring system memory 24 may comprise one or more computer-readable memories in communication with processors 22. Any computer-readable storage or memory for the purposes described herein may include any tangible medium that stores and/or participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media may include dynamic random access memory (DRAM), which typically constitutes a main memory.

Figure 2:
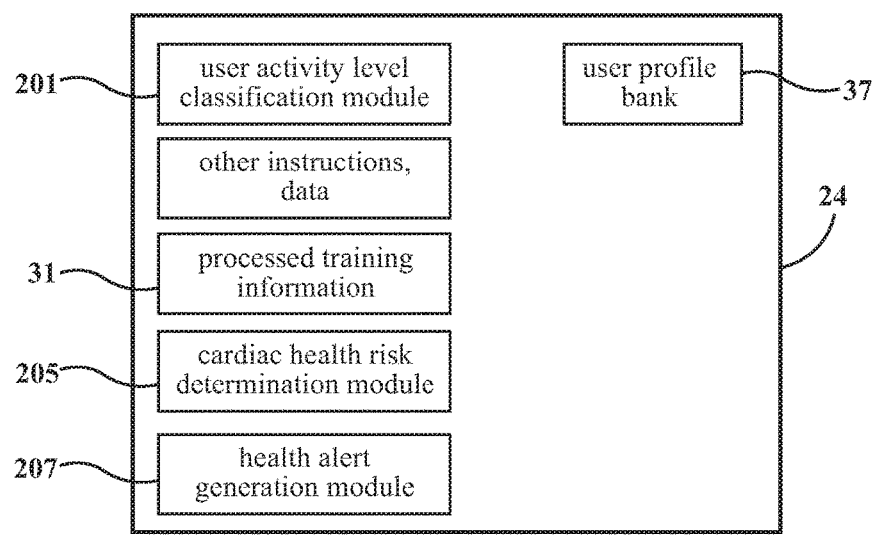
FIG. 2 is a schematic block diagram of a health monitoring system memory accordance with an embodiment described herein.

Referring now to FIG. 2, the health monitoring system memory 24 may contain data and/or instructions (e.g., program logic) executable by the processor(s) 22 to execute various functions of the health monitoring system. The memory 24 may contain additional instructions as well, including instructions to transmit data to, receive data from, interact with, or control one or more of the health monitoring system components described herein (for example, communications interface 27). The memory 24 may incorporate (or be in communication with) one or more buffers usable to store data such processed information and/or sensor data prior to processing by processors 22.

The memory 24 may also incorporate (or be in communication with) a database containing pulse rate data, values of previously calculated safe minimum and maximum pulse rates, mean pulse rates, and other pertinent parameter values gathered during previous uses of the health monitoring system by various users. This information may be stored in a file directory or user profile personalized to each individual user. The user profiles may be stored in a user profile bank 37 in memory 24 or in another location accessible by processors 22. A user profile may also contain information usable for identifying the individual user, physical characteristics such as height, most recent weight and body mass index (BMI) of a given user, and values of other parameters pertinent to the operations performed by the health monitoring system 19. Pulse rate and motion information from the current use session of the health monitoring system 19 by the user may also be stored in the user profile and/or buffered for use in calculations during operation of the system 19.

In one or more arrangements, the health monitoring system memory 24 may store a user activity level classification module 201 which may include instructions that, when executed by the one or more processors, cause the one or more processors to classify a current activity level of a user using motion information relating to the user. In one or more particular arrangements, the user is a current occupant (a driver or passenger) of a vehicle.

In one or more arrangements, the health monitoring system memory 24 may also store a cardiac health risk determination module 205 which may include instructions that, when executed by the one or more processors cause the one or more processors to determine if a current pulse rate of the user for the current activity level indicates a cardiac health risk to the user.

In one or more arrangements, the health monitoring system memory 24 may store a health alert generation module 207 which may include instructions that, when executed by the one or more processors, cause the one or more processors to, responsive to a determination that a current pulse rate of the user at the current activity level indicates a cardiac health risk to the user, generate one or more health alert signals.

General operation of embodiments of the health monitoring system will now be described, with reference to the drawings.

Figure 3:
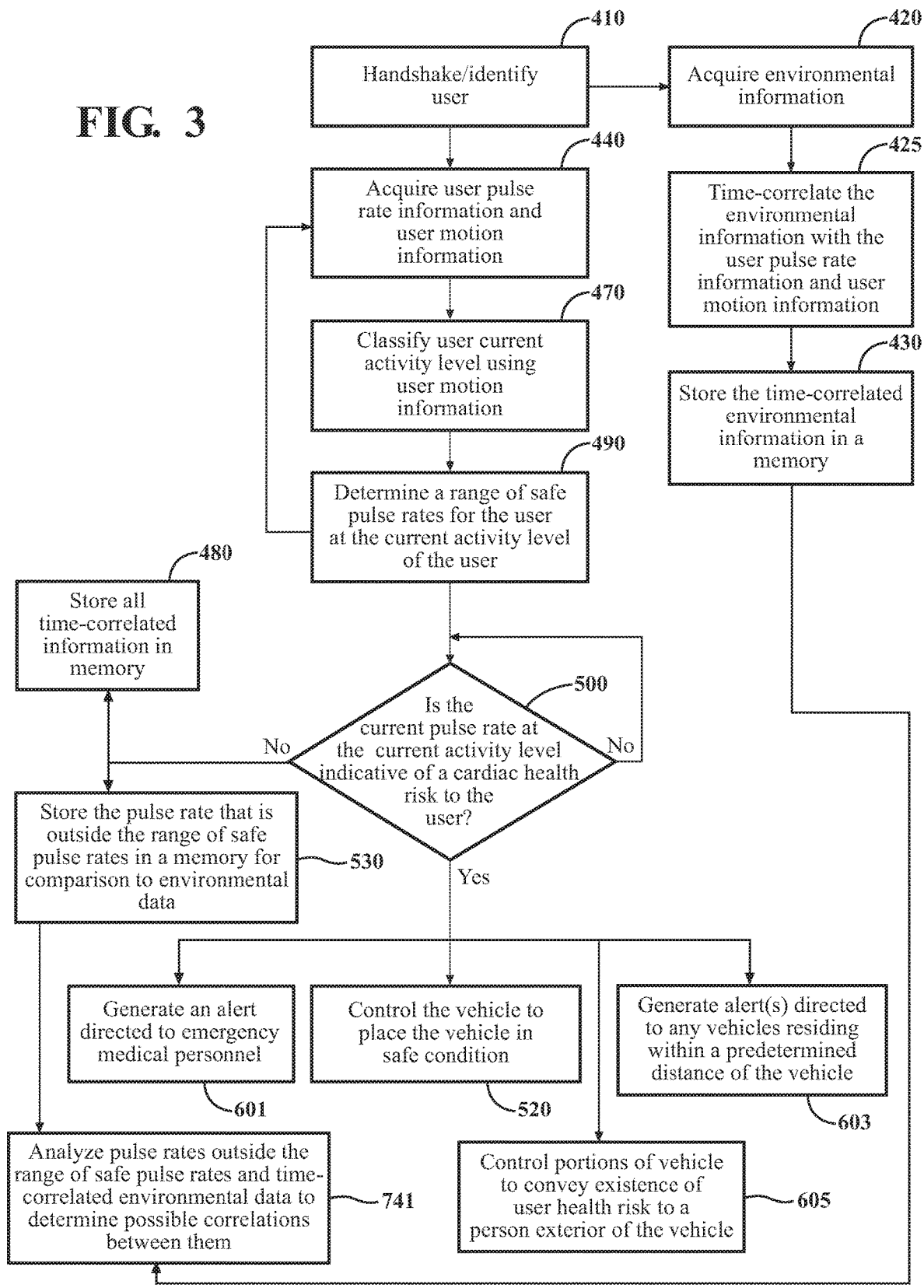
FIG. 3 is a flow diagram illustrating operation of a health monitoring system according to an embodiment described herein.

Referring to FIGS. 1, 2, and 3, prior to using the health monitoring system 19, a user may be operatively coupled to the health monitoring system. This may be done by attaching motion sensor(s) 20*a* and pulse rate sensors 20*b* to locations on the user so that the user's pulse rate and motion may be measured.

After attachment of the sensors to the user, the health monitoring system 19 may be activated. The system 19 may then (in block 410) implement one or more handshake or initialization procedures directed to identifying the current user and establishing communications between the health monitoring system sensors 20*a*, 20*b* and the processors 22. Any of a variety of user identification methods may be employed. For example, the health monitoring system 19 may query the user via a human machine interface (HMI) for identifying information. Alternatively, information acquired from a biometric sensor communicatively coupled to the health monitoring system processors 22 may be used to identify the user. Identification of the user as someone who has previously used the health monitoring system enables the system to access any stored pulse rate and motion information relating to the user. This enables stored information which is personal to the user to be used in determining more accurate safe minimum and maximum pulse rates for the user as described herein and also enables stored information particular to the current user to be employed in processing new incoming data, thereby providing more accurate results. Identification of the user also enables the user's existing information to be updated using new data acquired during the pending use session.

If the health monitoring system 19 cannot identify the current user as a former user or the system has no information stored on the current user, the health monitoring system may flag the user as a "new user". In this case, because past pulse rate and motion sensor information is not available, the health monitoring system may make certain assumptions in calculating initial values of various parameters used by the system during operation, as described herein. For a new user, the system may create or initialize a file directory or user profile as previously described, in which the user identity, sensor data, acquired and calculated parameters, and other information relating to the new user may be stored, during and after the current use session. The handshake procedures may also establish the communication between the sensors 20*a*, 20*b* and the system processors 22, and verify that the connection is working properly.

After communications between the sensors 20*a*, 20*b* and the processors 22 have been established, the health monitoring system 19 may (in block 440) acquire pulse rate information and motion information relating to the current user. Pulse rate information may include any information regarding current user pulse rate, information usable for calculating or determining pulse rate, and/or any information derived from or calculated by using pulse rate data. For example, the user's current pulse rate may be obtained from data from pulse rate sensor 20b. Motion information may include any information regarding motion of the current user and/or information derived from or calculated using parameters (for example, acceleration of portions of the user's body) which characterize and/or quantify user motion. In one or more arrangements described herein, user acceleration information may be used to quantify and classify the user's motion. User acceleration information may be in the form of data describing x, y, and z components of an acceleration of a portion of a body of the user during movement of the portion of the body at the current activity level of the user.

Pulse rate information and acceleration information may be continuously acquired and processed in a manner as described herein, so as to aid in detecting a potentially dangerous cardiac event as soon as possible. The use of "continuously" when referring to the reception, gathering, monitoring, processing, and/or determination of any data, information or other parameters described herein means that the these tasks are accomplished as soon as the relevant information exists or is detected, or as soon as possible in accordance with sensor acquisition and processor processing cycles.

Acquired pulse rate information may be time-correlated with acquired acceleration information (i.e., the acquired pulse rate and acceleration information may be tagged and/or stored such that any pulse rate information occurring at a time T1 may be associated (or associatable with) any acceleration information occurring at the same time T1). For example, the acquired pulse rate information and acceleration information may be time correlated during the data acquisition process, or coincident elements of pulse rate information and acceleration information may be time stamped after acquisition so as to indicate their simultaneity. This time-correlation of data enables analysis of the pulse rates associated with a given activity levels, and also analysis of how the pulse rates may vary according to activity level for an individual user. The time-correlated information may pulse rate information and acceleration information may be analyzed using the machine learning algorithms described herein to improve provide a more accurate user profile Also, after system initialization, environmental information may be acquired (in block 420) simultaneously with the acquisition of user pulse rate and motion information. Environmental information may be acquired using various sensors configured for measuring and/or detecting various aspects of the user's environment. In one or more particular arrangements, the sensors may be sensors incorporated into a vehicle and configured for detecting and/or measuring aspects of the vehicle's surroundings, such as temperature, the proximity the vehicle to other vehicles or pedestrians, pending or possible contact or collision between the vehicle and other vehicles or objects, and numerous other aspects. However, any of a wide variety of sensors may be used to detect one or more environmental parameters which are deemed to have a possible effect on user pulse rate.

For example, one or more cameras may be operable to register and/or record images of the user's face during operation of the health monitoring system. These images may be monitored or studied for indications of stress which may be time-correlated with changes in pulse rate, environmental occurrences, and other information. Also, one or more microphones may be provided for recording sounds made by the user and/or occurring in the user's environment. This sound information may also be time-correlated with changes in pulse rate, environmental occurrences, and other information. This correlated information may be processed by machine-learning algorithms to help establish connections between environmental factors and variations in pulse rate. Data from other sensors (such as radar, lidar, and cameras) may also time-correlated with the changes in pulse rate, environmental occurrences, and other information to aid in establishing and clarifying connections or correlations between pulse rate and environmental factors.

In block 425, the environmental information may be time-correlated with the pulse rate and motion information in the manner described herein. The time-correlated environmental information may be stored in a memory in block 430. The time-correlated environmental information may later (in block 741) be analyzed in conjunction with the associated pulse rate information in an attempt to detect connections between occurrences in the environment and fluctuations in user pulse rate.

Returning to block 440, after receipt of user acceleration data, the health monitoring system processors 22 may (in block 470), using logic stored in the user activity level classification module 201, analyze the user acceleration data for use in classifying or categorizing a current activity level of the user into one of a plurality of predetermined activity levels. A user "activity level" may relate to such factors as the extent and/or rapidity of motion of a portion of the user to which the motion sensor is attached, the rate of change of direction of motion, and/or other parameters. In embodiments described herein, the activity level may be reflected by the acceleration data relating to the user. For example, relatively higher values of one or more of the acceleration components $a_x$, $a_y$, $a_z$ will generally be indicative of a relatively higher user activity level. Similarly, relatively higher values of the resultant acceleration A (described below) and/or the mean resultant acceleration $A_m$ (also described below) will generally be indicative of a relatively higher user activity level. In addition, the activity level as indicated by the motion sensor(s) 20a will generally correspond to the pulse rate of the user under normal conditions (e.g., a relatively higher user activity level will be reflected in a relatively higher pulse rate). Thus, one possible indicator of a dangerous cardiac event may be a spike in pulse rate without an accompanying or corresponding increase in user activity level.

In one or more arrangements, the current activity level of the user may be classified into one of a low activity level, a moderate activity level, and a high activity level, based on the acceleration data relating to the user. The possible user activity levels may be defined in any of a variety of ways. For example, the health monitoring system may be "trained" prior to operation by processing a training data set and basing the activity level classifications on the results of processing the training data set. Results of processing the training data set may be stored in a processed training information block 31 in (or in communication with) the health monitoring system memory 24, so that this information may be accessed by processors 22 during operation of the health monitoring system. The processed training information may include acceleration and pulse rate information gathered from numerous users engaging in activities classed as relatively low activity level activities (e.g., sitting, sleeping), activities classed as relatively moderate activity level activities (e.g., walking, light housework), and activities classed as relatively high activity level activities (e.g., running, sustained physical exercise). The training data may include data for various user parameters which may be pertinent to pulse rate, such as body mass index (BMI), age, sex, geographical location, medical history, levels of smoking and alcohol consumption, degree of athletic activity, etc. The acceleration sensor(s) may measure the accelerations of a portion of the body to which the sensor(s) are attached and the pulse rate sensor may measure associated pulse rates. The acceleration sensor and associated pulse rate data may be time-correlated so that the pulse rate associated with a given acceleration reading is known. Values of these parameters may be time-correlated with associated user training data pulse rates and motion information to determine how pulse rates may vary according to various personal and environmental factors.

The acceleration sensor and associated pulse rate data may also be time-correlated and/or otherwise associated with the other information affecting pulse rate. This enables machine-learning and/or other analysis of how factors such as body mass index (BMI), age, sex, geographical location, medical history, levels of smoking and alcohol consumption, etc. may affect pulse rates at various activity levels. Analysis of training information in this manner may provide correlations between parameters which may be applied to new users of the health monitoring system to help tune or adjust boundaries of user activity levels, and to increase the accuracy of the safe pulse rates determined as described herein, for a particular user. For example, correlations detected between BMI and pulse rate in the training data may also be applied to data relating to new users of the health monitoring system.

Processing of the training data set prior to actual use of the health monitoring system may also provide a basis for delineating between user activity levels based on acceleration data. Processing of the training data set may also show how pulse rate data may correlate with acceleration data during actual use of the health monitoring system. The results of processing the training data set may be used to define boundaries for the user activity level classifications.

Although the present disclosure describes one or more methods for establishing user activity level classifications and methods for classifying user activity level based on user acceleration data, alternative activity level classes and/or methods of user activity level classification definition may also be used.

In one example of establishing user activity level classifications, for processing of acceleration data during system training and during actual use of the health monitoring system, a resultant acceleration A may be defined for each acceleration data point. The resultant acceleration A may represent a composite of the individual values of the x, y, and z acceleration components for the given acceleration data point:

$$A = \sqrt{a_x^2 + a_y^2 + a_z^2}$$

where:
  $a_x$=an x-component of a given acceleration sensor reading;
  $a_y$=a y-component of the acceleration sensor reading; and
  $a_z$=a z-component of the acceleration sensor reading.

The activity levels used for classification may be defined according to the resultant acceleration values A derived from the training data set (i.e., mutually exclusive ranges of resultant acceleration values A may be established for defining low, moderate, and high activity levels). For example, in one or more arrangements, based on processing of a training data set, the total range of resultant acceleration values A may be divided into three sub-ranges (0-a1, a1-a2, and a2-a3), with 0<a1<a2<a3, and each sub-range defining an associated user activity level (low, moderate, or high).

In one or more arrangements, user activity levels generating resultant acceleration values A in within a range of 0<=A<a1 may be classified as low activity levels. User activity levels generating resultant acceleration values A in within a range of a1<=A<a2 may be classified as moderate activity levels. User activity levels generating resultant acceleration values A in within a range of a2<=A<=a3 may be classified as high activity levels. Thus, the value a1 may serve as an upper boundary of the low activity level, the values a1 and a2 may serve as lower and upper boundaries, respectively, of the moderate activity level, and the values a2 and a3 may serve as lower and upper boundaries, respectively, of the high activity level.

Classification of the user's current activity lever may aid in tailoring the health monitoring system to particular users, especially users for which a single activity level predominates. For example, as more data is gathered for a particular user at a given user activity level, a more accurate picture of the user's pulse rate range at that activity level is determined, and more accurate determinations of the maximum and minimum safe pulse rates for the user may be determined for use in detecting cardiac events, in the manner described herein. Also, sudden spikes in the user's pulse rate which may be indicative of a medical emergency may be more easily identifiable for a particular user if the normal pulse rates for the particular user are calculated using a greater amount of data. This is important because a cardiac event may occur at any user activity level. The amount of data for a particular user may be accumulated over time during use of the health monitoring system by the user.

Any of a variety of methods may be used to classify the user current activity level into one of the pre-defined classifications, based on the user acceleration data. In one example, user acceleration data and pulse rate data may be acquired over a predetermined time period (for example, one minute), to provide a discrete block of acceleration data and pulse rate data. The block acceleration data may be processed to generate a resultant acceleration value A for each acquired acceleration data point (comprising components $a_x$, $a_y$, $a_z$), as previously described. The mean $A_m$ of the resultant acceleration values A from the block of acceleration data may be determined from the relationship:

$$A_m = \sum_{i=1}^{n} A_i$$

where $A_i$=an ith resultant acceleration value; and
  N=a total number or resultant acceleration values derived from the block of acceleration data.

A standard deviation σ of the resultant acceleration values A from the block of acceleration data may be determined from the relationship:

$$\sigma = \sqrt{\frac{1}{N} \sum_{i=1}^{N} (A_i - A_m)^2}$$

Using the mean and standard deviation as calculated above, the user activity level may be classified based on the block of acceleration data. Then, in the example described above where the user activity level boundaries are 0, a1, a2, and a3, the current user activity level (based on the block of acceleration data) may be classified as low, moderate, or high activity based on the following:

if $0<(A_m+2\sigma)<a1$, classify activity level as low;
if $a1<=(A_m+2\sigma)<a2$, classify activity level as moderate; and
if $a2<=(A_m+2\sigma)<a3$, classify activity level as high.

This scheme reflects the fact that the mean resultant acceleration $A_m$ will increase as the activity level increases. Statistically, 95.8% of the data values in the block of acceleration data should lie within $2\sigma$ of the mean $A_m$.

In one or more arrangements, using the classification scheme set forth herein, the user activity level classification may shift dynamically during a single session of use by a user, as the acceleration data is continuously acquired and processed. For example, as the user activity level (as reflected in increased resultant acceleration values A) increases during use, the user activity level may be dynamically reclassified from a relatively lower activity level to a relatively higher activity level based on processing of the relatively higher resultant acceleration values A.

As stated previously, acquired data, processed data and various parameters relating to a particular user may be stored in one or more files forming a profile for the user. The user profile and other information relating to the user may be stored in a memory, such as a memory of the health monitoring system or other memory.

In addition, the initially assigned boundaries delineating the low, moderate, and high activity levels may be varied for a given user over time, to account for changes in the individual's health and/or environment. In one or more arrangements, the health monitoring system processors 22 may incorporate (or be in communication with) artificial or computational intelligence elements (e.g., neural network) or other machine learning algorithms, generally designated 21 (FIG. 1). The processors 22 may use machine learning algorithms 21 in processing user pulse rate data, motion data, physiological and environmental data, as well as updated personal information to adjust or personalize the boundaries of the activity level classifications according to the given user. Different weights may be applied to various types of information usable in determining the activity level boundaries. For example, as a greater amount of information relating to a given user is acquired over time, information relating to the given user may be assigned a greater weight than training information relating to subjects from which general training data was acquired. Also, more recent information relating to the given user may be given greater weight that older information relating to the given user.

Referring again to FIG. 3, after classification of the user current activity level, the health monitoring system may (in block 490), using logic stored in the cardiac health risk determination module 205, determine a range of safe pulse rates for the user at the current activity level of the user. Because the pulse rate depends on various factors which may vary according to the individual user, it is desirable to personalize operation of the health monitoring system according to the particular user.

Figures 4, 4A:
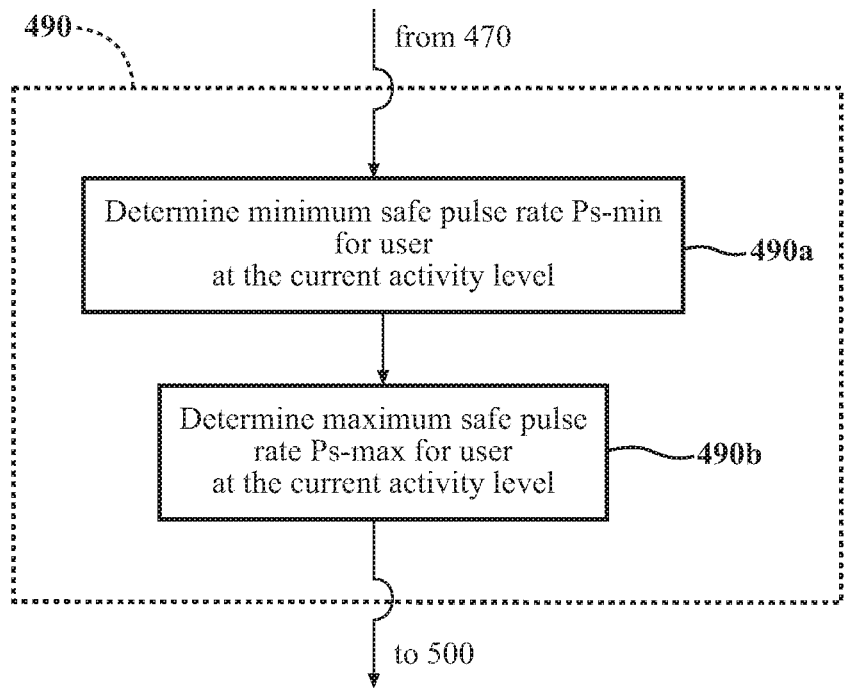
FIG. 4 is a flow diagram showing, in greater detail, an embodiment of one of the operational steps shown in FIG. 3.
FIG. 4A is a table containing exemplary age-dependent values of maximum and minimum safe pulse rates.

Referring now to FIG. 4, in one or more arrangements, determination of the range of safe pulse rates for the particular user (as described with regard to block 490 of FIG. 3) may comprise determining (in block 490*a*) a safe minimum pulse rate for the user at the current activity level of the user, and determining (in block 490*b*) a safe maximum pulse rate for the user at the current activity level of the user. "Determining" safe pulse rates or a range of safe pulse rates may include accessing the safe pulse rate and/or range from a memory and/or calculating the safe pulse rate and/or range using various parameters and/or any of a variety of methods.

The safe pulse rates for a user may be dependent on factors such as age, sex, and body mass index (BMI). For example, according to various sources, a safe pulse rate for a healthy person while exercising is between 50% of (220 beats per minute—age) and 85% of (220 beats per minute—age). In addition, some studies have determined that, if a user's heart rate is above 220 beats per minute for more than one minute, heart muscle damage and arrhythmia may result. In one or more arrangements, for a new user of the health monitoring system, with no profile or previous user pulse rate data on record, the minimum and maximum safe pulse rates may be determined using the following formulae:

Maximumpulserate=220−(age)
Minimumpulseratedurinexcercise=0.5(220−(age))
Maximumpulserateduringexcercise=0.85(220−(age))
Maximumpulserate$_{sustained}$<220 where:

Maximumpulserate=the maximum safe pulse rate of a user at rest, based on age;
Minimumpulseratedurinexcercise=the minimum safe pulse rate of a user during exercise, based on age;
Maximumpulserateduringexcercise=the maximum safe pulse rate of a user during exercise, based on age; and
Maximumpulserate$_{sustained}$=the maximum pulse rate that may be sustained for no more than one minute without possible heart muscle damage.

In another arrangement, the new user's age may be used in conjunction with the information provided in FIG. 4A to determine initial values of maximum and minimum safe pulse rates.

In one or more arrangements, machine learning algorithms 21 may assist in determining a safe pulse rate or a range of safe pulse rates for a new user. For example, a new user may input personal information such as height, weight, medical history information, information relating to smoking and alcohol consumption, and other information regarding parameters affecting pulse-rate. By processing the new user information in conjunction with results of previous analyses of training data relevant to pulse-rate, including using any correlations between pulse rate and height, weight, medical history information, etc., determined by the machine learning algorithms 21, the algorithms 21 may be able to determine an initial safe pulse rate more tailored to the individual user, and which may result in more effective operation of the health monitoring system for the user.

For a previous user of the health monitoring system, with pulse rate and acceleration information from previous use(s) stored in the system, the minimum and maximum safe pulse rates Safemin and Safemax for the current use session may be determined using the relationships below:

Safemin=(NewMean+Minimum Pulse rate)/2
Safemax=(NewMean+Maximum Pulse rate)/2 where:

Safemax=the maximum safe pulse rate for the current user at the current activity level;
Safemin=the minimum safe pulse rate for the current user at the current activity level;
NewMean=a new (or updated) mean pulse rate updated after new pulse rate data is acquired during the current use session;

Minimum Pulse Rate=Minimum pulse rate at the user's current activity level; and

Maximum Pulse Rate=Maximum pulse rate at the user's current activity level.

The parameter NewMean may be calculated and updated per the individual user using the relationship:

NewMean=(Mean×No+24_mean)/(No+1)

where:
Mean=the mean pulse rate calculated using all previous data acquired for the current user at the current activity level;
No=a total number of days over which pulse rate data has been acquired for the current user at the current activity level; and
24_mean=a mean pulse rate calculated based on pulse rate data stored during the most recent 24 hours of use of the device by the current user.

The minimum pulse rate at the user's current activity level may be taken as the minimum pulse rate from the first block of pulse rate data taken at the current activity level during the current use session. Similarly, the maximum pulse rate at the user's current activity level may be taken as the maximum pulse rate from the first block of pulse rate data taken at the current activity level during the current use session. As the user's activity level classification changes based on changes in the user's activity, the parameters Safemin and Safemax may be recalculated using pulse rate data acquired as soon as the user enters the new current activity level, and using data for the user from the previous use session and at the new current activity level. In this manner, the minimum and maximum safe pulse rate values for the user at a given activity level may be recalculated according to variations in the activity level. Stated another way, a mean pulse rate NewMean for the current user may be calculated for each different activity level of the user. In addition, this mean pulse rate may be used to determine values of the parameters Safemax and Safemin as described above, for the current activity level. Thus, if the user's activity level shifts to a new classification during a single use session, the parameters NewMean, Safemax and Safemin may be recalculated for the new user activity level. In addition, Safemax, Safemin, and other parameters used in the cardiac risk analysis may be affected by changes in the boundaries of the activity levels for a given user. These changes may occur as a result of machine-leaning analysis of the pulse rate, acceleration, environmental, and other data relating to the user, and the machine-learning algorithms operate to tailor the parameter values to the individual user.

Referring now to FIGS. 3 and 5, after the minimum and maximum safe pulse rates for the user at the current user activity level have been determined, and during continuous acquisition and processing of pulse rate data, the health monitoring system may (in block 500) determine, using the range of safe pulse rates for the user and logic stored in the cardiac health risk determination module 205, if and when a current pulse rate of the user is indicative of a cardiac health risk to the user. The cardiac health risk determination module 205 may include instructions that when executed by the one or more processors cause the one or more processors to: determine when the current pulse rate of the user is outside the range of safe pulse rates; responsive to a determination that the current pulse rate of the user is outside the range of safe pulse rates, determine if a difference between the current pulse rate of the user and a second most recent pulse rate exceeds a predetermined threshold value; responsive to a determination that the difference between the current pulse rate of the user and the second most recent pulse rate exceeds the predetermined threshold value, determine if a difference between the second most recent pulse rate and a third most recent pulse rate exceeds the predetermined threshold value; and, responsive to a determination that a difference between the second most recent pulse rate and the third most recent pulse rate exceeds the predetermined threshold value, determine that the current pulse rate of the user is indicative of a cardiac health risk to the user.

For purposes of determining if a current pulse rate of the user is indicative of a cardiac health risk to the user, the current pulse rate of the user is taken as the most recently determined (i.e., measured or calculated) pulse rate. Also, the "second most recent pulse rate" is considered to be the pulse rate determined prior to the determination of the current pulse rate of the user. In addition, the "third most recent pulse rate" is considered to be the pulse rate determined prior to the determination of the second most recent pulse rate. Also, the pulse rate may be recalculated or updated every second, using data acquired from the previous sixty seconds. If sixty seconds worth of data is not yet available, a pulse rate may be interpolated using the available data until sixty seconds worth of data is available. For example, the number of pulses from fifteen seconds of available pulse rate data may be multiplied by four to provide an approximated, temporary current pulse rate. A spike in the calculated pulse rate over the one second interval between successive pulse rate calculations may be determined by comparison of successive pulse rates as described herein. Also, if desired, the pulse rate may be calculated using a time interval other than one minute.

Figure 6:
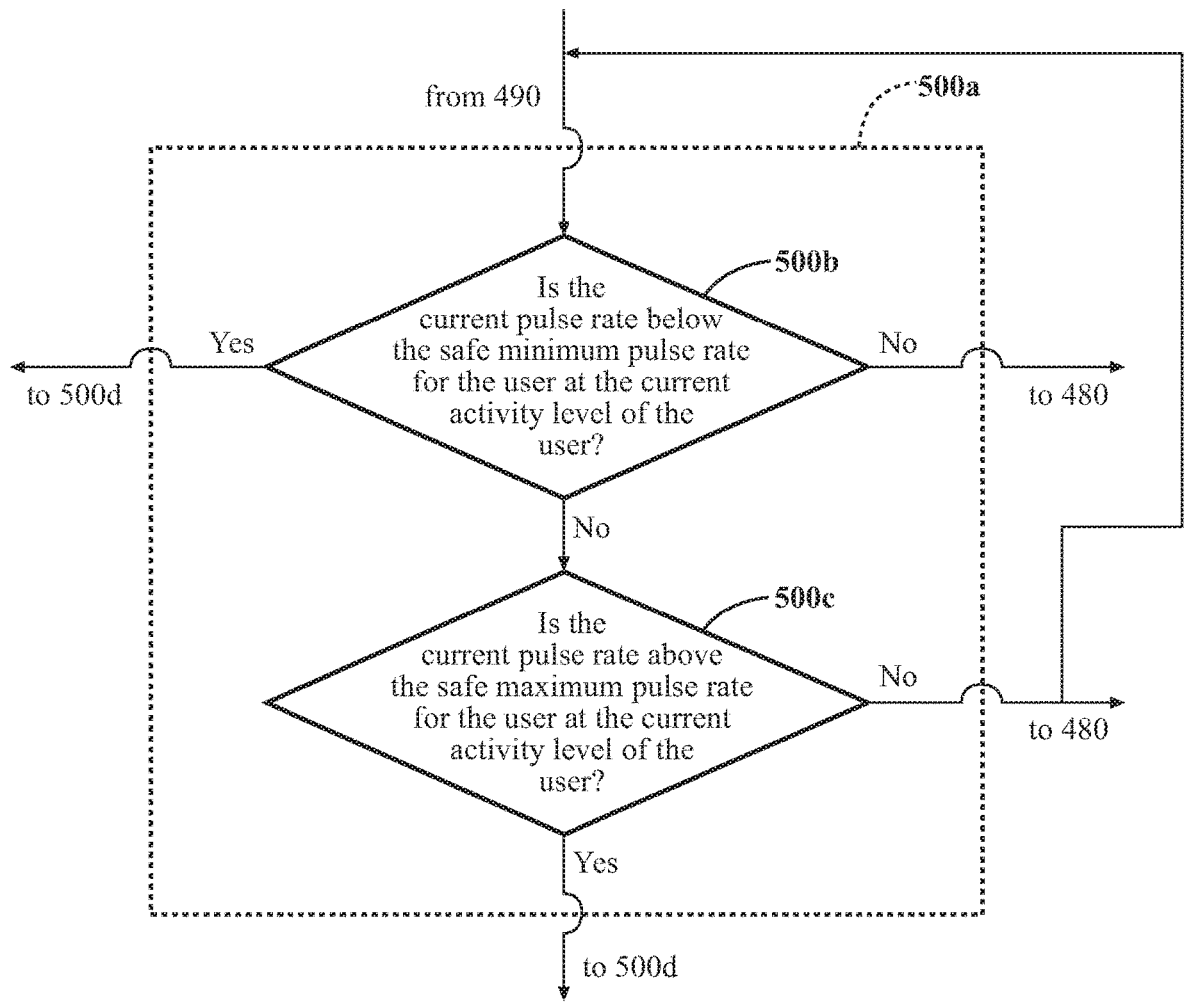
FIG. 6 is a flow diagram showing, in greater detail, an embodiment of the operational steps shown in FIG. 5.

Referring to FIGS. 5 and 6, to determine when the current pulse rate of the user is indicative of a cardiac health risk to the user, the health monitoring system may (in block 500*a*) determine when the current pulse rate of the user is outside the range of safe pulse rates previously determined. To determine when the current pulse rate of the user is outside the range of safe pulse rates, the health monitoring system may (in block 500*b*) (FIG. 6) evaluate the current pulse rate of the user to determine if the current pulse rate of the user is below the safe minimum pulse rate for the user at the current activity level of the user. If the current pulse rate of the user is determined to be below the safe minimum pulse rate for the user at the current activity level of the user, control may transfer to block 500*d*, which initiates a comparison between the current pulse rate of the user and the most recent two previous pulse rates, as described in greater detail below. If the current pulse rate of the user is determined not to be below the safe minimum pulse rate for the user at the current activity level of the user, control may transfer to block 500*c*, which determines if the current pulse rate of the user is above the safe maximum pulse rate for the user at the current activity level of the user. If the current pulse rate of the user is determined not to be above the safe maximum pulse rate for the user at the current activity level of the user, control may transfer to block 480, in which time-correlated pulse rate and acceleration information may be stored in a memory for further analysis and/or in later use sessions by the current user. However, if the current pulse rate of the user is determined in block 500*c* to be above the safe maximum pulse rate for the user at the current activity level of the user, control may transfer to block 500*d* (FIG. 5), which initiates the comparison between the current pulse rate of the user and the most recent two previous pulse rates, as described in greater detail below.

Referring to FIG. 5, in block 500*d*, responsive to a determination in block 500*a* that the current pulse rate is outside the range of safe pulse rates, the system may determine if a difference between the current pulse rate of the user and the second most recent pulse rate of the user exceeds a predetermined threshold value, according to the relationship:

$$|P_c - P_{c-1}| > \frac{|SafeMax - SafeMin|}{2}$$

where $P_c$=the current pulse rate of the user; and $P_{c-1}$=the second most recent pulse rate (i.e., the pulse rate before recalculation using the latest data to provide the current pulse rate of the user).

Thus, in one or more arrangements, the threshold value may be defined by the relationship:

$$\frac{|SafeMax - SafeMin|}{2}$$

In block 500d, if a difference between the current pulse rate of the user and the second most recent pulse rate does not exceed the predetermined threshold value, control may transfer to block 530, where the pulse rate determined to be outside the range of safe pulse rates may be stored in a memory for comparison (in block 741) to time-correlated environmental data. The time-correlated environmental data and pulse rate data may be analyzed to attempt to determine possible connections between the pulse rate(s) outside the safe limits and environmental events detected as occurring at the same time as the pulse rate(s) outside the safe limits. However, if the difference between the current pulse rate of the user and the second most recent pulse rate exceeds the predetermined threshold value, control may transfer to block 500e, where the system may determine if a difference between the second most recent pulse rate and the third most recent pulse rate also exceeds the predetermined threshold value, according to the relationship:

$$|P_{c-1} - P_{c-2}| > \frac{|SafeMax - SafeMin|}{2}$$

where $P_{c-2}$=the third most recent pulse rate.

In block 500e, if the difference between the second most recent pulse rate and the third most recent pulse rate does not exceed the predetermined threshold value, control may transfer to block 530, where the pulse rate determined to be outside the range of safe pulse rates may be stored in a matrix for comparison to the time-correlated environmental data. However, if the difference between the second most recent pulse rate and the third most recent pulse rate exceeds the predetermined threshold value, the current pulse rate of the user is determined to indicate a cardiac health risk to the user.

The threshold value described above is indicative of a severity of the change in pulse rate over the time period between successive pulse rate measurements. The threshold value is defined so that a pulse rate exceeding the threshold twice during the span of three successive pulse rate measurements indicates a sustained change in pulse rate that is so severe that it is deemed to constitute a medical emergency warranting generation of a health alert. Thus, the current pulse rate of the user may be considered indicative of a cardiac health risk to the user because the current pulse rate indicates a change from the second most recent pulse rate sufficient to exceed the predetermined threshold, and because this change immediately follows a condition in which the change from the third most recent pulse rate to the second most recent pulse rate also exceeded the predetermined threshold value. Because the above relationships use the absolute values of the changes in pulse rate and the difference between minimum and maximum pulse rates, the system will register both a severe drop in pulse rate during the span of the three successive pulse measurements, and also a severe rise or spike in pulse rate during the span of the three successive pulse measurements. In addition, as stronger correlations between sudden changes in pulse rate and other parameters (such as stress indications in a user's facial expression, environmental factors, etc.) are established by machine learning and/or other data analysis, values of these parameters during the severe spike in pulse rate may be used as further evidence of a cardiac risk to the user, and may even factor into the decision to generate medical alerts.

In one or more alternative methods for determining a predetermined threshold value more tailored to an individual user, the threshold value may be determined by analyzing pulse rate data which lies outside the safe pulse range, but which does not satisfy the requirement that the difference between the second most recent pulse rate and the third most recent pulse rate exceeds the predetermined threshold value. After verifying with medical personnel that the presence of such data with respect to the user does not indicate a serious cardiac problem in the user, machine learning algorithms 21 may utilize such data in determining a predetermined threshold value for the individual user. In determining a predetermined threshold value for the individual user, machine learning algorithms 21 may also take into consideration other available information relating to pulse rate and personal to the individual user, including BMI, age, sex, medical history, etc.

Thus, as shown in FIGS. 5 and 6, the health monitoring system may (in block 500a) continuously check, based on the latest pulse rate data, whether the current pulse rate of the user is outside the range of safe pulse rates. If the current pulse rate of the user is outside the range of safe pulse rates, the system may proceed to the next analysis steps (blocks 500d and 500e) to determine if the current pulse rate of the user indicates a cardiac health risk to the user at the current activity level. Also, as seen in FIG. 3, the health monitoring system may be configured to continuously execute blocks 440, 470, 490 to acquire pulse rate and acceleration data (block 440), update the user current activity level (block 470), and update the range of safe pulse rates for the user (block 490). The latest safe pulse rates are then continuously used to determine (in block 500) if the current pulse rate of the user indicates a cardiac health risk to the user at the current activity level. If there are no changes to the user activity level based on acceleration data, and no changes to the minimum and maximum safe pulse rates. the system will continue (in block 500) to process the latest pulse rate data for the user at the current activity level, to determine if and when a current pulse rate of the user indicative of a cardiac health risk to the user occurs.

Referring again to FIG. 3, responsive to a determination that a cardiac health risk exists to the user at the current activity level, and using logic stored in the health alert generation module 207, the health monitoring system may generate (in block 601) one or more health alerts. For example, the health monitoring system may generate one or more alerts directed to emergency medical personnel or emergency services 97. The health monitoring system may generate one or more alerts directed to mobile or cellular devices 98 (for example, devices of family members and/or friends of the user).

FIG. 3 also shows various steps which may be performed in a particular embodiment of the health monitoring system configured for use in a vehicle, responsive to a determination that a cardiac health risk exists to a user who is an occupant of the vehicle. Referring to FIG. 3, in one or more arrangements, and responsive to a determination that the current pulse rate of the vehicle occupant indicates a cardiac health risk to the occupant, a vehicle computing system of the occupant's vehicle may (in block 605) control portions of the occupant's vehicle so as to generate visible and/or audible alerts to pedestrians and occupants of other, nearby vehicles. As an example, and with reference to FIG. 7, a vehicle computing system 14 (described in greater detail below) may be configured to execute instructions stored in a memory to autonomously control the occupant's vehicle to intermittently flash vehicle headlights/highbeams 73 on and off responsive to receipt of the health alert signal from the health monitoring system, as a warning to pedestrians and/or drivers of other vehicles. Also, the vehicle horn 75 may be operated to attract the attention of pedestrians and/or surrounding vehicles in an attempt to obtain assistance for the vehicle occupant experiencing the cardiac condition. Also, any other element or system of the occupant's vehicle which may be used to generate a human-perceivable indicator of a potentially dangerous medical condition occurring in the vehicle may be configured for autonomous operation or control by the occupant's vehicle. As used herein, the term "perceivable" is understood to mean detectible by one or more human senses, such as sight or hearing, by a person exterior of the occupant's vehicle. The person exterior of the occupant's vehicle may be, for example, a pedestrian or an occupant of another vehicle on the road near the occupant's vehicle.

In one or more arrangements, a vehicle computing system may also control operation of the vehicle so as to autonomously drive the vehicle. Referring again to FIG. 3, responsive to a determination that the current pulse rate of a vehicle occupant indicates a cardiac health risk to the occupant, and in an embodiment in which the health monitoring system is incorporated into and/or used in a vehicle with the driver or other vehicle occupant as the user, the vehicle computing system may (in block 520) generate commands for controlling the occupant's vehicle to place the vehicle in a safe condition. Placing of the occupant's vehicle in a safe condition may include, for example, autonomously operating the steering, throttle, braking and other vehicle systems to steer the occupant's vehicle off a road, and stopping the vehicle when the vehicle is out of traffic. In another example, the vehicle computing system may be configured to execute instructions stored in a memory to control the occupant's vehicle to autonomously drive the vehicle to a user-selected location residing within a predetermined distance of the vehicle when the health alert signal is generated. The user-selected location may be programmed into the vehicle computing system or navigation system. The vehicle computing system may be configured to activate a vehicle self-driving program directed to driving the occupant's vehicle to the user-selected location upon receipt of a health alert signal from the health monitoring system, and after a determination by the vehicle computing system and/or navigation system that the user-selected location currently resides within the predetermined distance of the occupant's vehicle. The vehicle computing system may be configured to continuously determine and monitor a driving situation or environment of the occupant's vehicle, using information from the various vehicle internal sources such as vehicle sensors and/or a navigation system, from external sources such as other vehicles (via a V2V communications network) or a cloud computing environment, and/or from other sources.

Vehicle sensors may also be configured to detect other vehicles residing within a predetermined distance of the occupant's vehicle. The other vehicles may be constantly detected and monitored. The health alerts may be transmitted over a V2V communications network. Referring again to FIG. 3, responsive to a determination that the current pulse rate of a vehicle occupant indicates a cardiac health risk to the occupant, one or more signals (in block 603) may be generated by the occupant's vehicle for transmission (via the V2V communications network) to other vehicles alerting them to the fact that a health emergency is occurring in the occupant's vehicle. This may enable drivers of the other vehicles to maneuver their vehicles so as to distance themselves from the occupant's vehicle. Depending on the configuration of the occupant's vehicle, the alert signals to other vehicles may be generated by the health monitoring system 19 or by a vehicle computing system in operative communication with the health monitoring system 19, or incorporating elements of the health monitoring system 19.

Referring now to FIGS. 7-10, and as previously described, an embodiment the health monitoring system may be configured to operate in (or be incorporated into) a vehicle, with an occupant of the vehicle as the user. In one or more arrangements, the vehicle may be configured for autonomous or semi-autonomous control. An embodiment of the health monitoring system configured for operation in a vehicle environment may operate in the manner previously described with regard to FIGS. 3-6. In addition, an embodiment of the health monitoring system configured for operation in a vehicle environment may perform additional functions, such as generating additional, different types of alerts and prompting autonomous control of one or more aspects of vehicle operation, as described in greater detail below.

FIG. 7 is a schematic block diagram of a vehicle incorporating an embodiment of a health monitoring system as previously described, configured for operating in a vehicle. The health monitoring system may be configured for monitoring a pulse rate of a user in the manner previously described. The health monitoring system may be configured for generating a health alert when the system determines that a current pulse rate of the occupant indicates a cardiac health risk to the occupant. The vehicle 11 may take the form of a car, truck, or any other vehicle capable of performing the operations described herein. The vehicle 11 may be configured for autonomous operation, and may operate in a fully or partially autonomous mode. While in an autonomous mode, the vehicle 11 may be configured to operate without human interaction. For example, in a mode in which operation of the vehicle 11 is autonomously controlled to place the vehicle in a safe condition when a pulse rate indicating a cardiac health risk to the occupant occurs, the vehicle may be autonomously controlled to operate the throttle, braking, steering, headlights, and/or other vehicle systems and elements so as to place the vehicle in a safe condition, in case the occupant is a driver and is too debilitated to safely operate the vehicle.

The vehicle 11 may also be configured for completely autonomous driving operations (i.e., for self-driving, without the presence of a driver or driver input) from a start location to a given or predetermined destination along a route determined by a navigation unit or system 23, for example. The vehicle 11 may include various systems, subsystems and components in operative communication with each other, such as a sensor system or array 28, a vehicle computing system 14, one or more vehicle communications interfaces 16, a steering system 18, a throttle system 29, a braking system 25, a motive power system 26, and other systems and components needed for operating the vehicle as described herein. The vehicle 11 may include more or fewer subsystems than those shown in FIG. 7, and each subsystem could include multiple elements. Further, each of the subsystems and elements of vehicle 11 may be interconnected. Performance of one or more of the described functions of the vehicle 11 may be executed by multiple vehicle systems and/or components operating in conjunction with each other. The various vehicle systems may be controlled by (or may otherwise interact with) the vehicle computing system 14.

FIG. 7 also shows a schematic arrangement of primary control sub-systems 18, 25, 26, 29 of the vehicle 11 configured to enable full or partially autonomous control of the vehicle 11, for the purposes described herein. The primary control sub-systems may be communicatively coupled to computing system 14, sensor system 28, navigation system 23, and other systems and/or components of the vehicle as needed via a suitable CAN bus 33 or using any other suitable method, whether wired or wireless. The vehicle embodiment shown in FIG. 7 includes four primary control sub-systems (a steering control system 18, a braking control system 25, a motive power control system 26, and a throttle control system 29). FIG. 7 shows just a few examples of vehicle sub-systems 18, 25, 26, 29 which may be incorporated into a vehicle. A particular vehicle may incorporate one or more of these systems or other systems (not shown) in addition to one or more of the systems shown.

A "primary control sub-system" is a system designed to effect control and operation of one of the primary vehicle controls (i.e., brake, steering, throttle, and motive power), as described herein. Each of primary control sub-systems 18, 25, 26, 29 may be configured for fully or partially autonomous operation under the direction of an associated controller (not shown) specialized for the control of the sub-system. For example, a braking system 25 may include a specialized braking system controller (not shown) and various actuatable elements (brakes, etc.) (not shown) necessary for executing braking control commands, and which are configured to be operable responsive to control commands received from the braking controller. Steering system 18 may include a specialized steering system controller (not shown) in operative communication with associated actuatable steering components (not shown) necessary for executing steering control commands. Throttle system 29 may include a specialized throttle controller (not shown) in operative communication with associated actuatable throttle components (not shown) necessary for executing throttle control commands. Motive power system 26 may include a specialized motive power system controller (not shown) in operative communication with associated actuatable motive power components (not shown) necessary for executing motive power control commands. Alternatively, one or more of the primary control sub-systems 18, 25, 26, 29 may be configured for full or partially autonomous control by vehicle computing system 14, for controlling the vehicle for the purposes described herein.

The steering system 18 may include such elements as the vehicle wheels, servo-mechanisms, gears, steering knuckles, and/or any other elements or combination of elements (including any computer system-controllable mechanisms or elements) that may be operable to enable autonomous adjustment of the heading of vehicle 11. The braking system 25 may include any combination of elements and/or any computer system-controllable mechanisms configured to decelerate the vehicle 11. The motive power system 26 may include components operable to provide powered motion for the vehicle 11. In an example embodiment, the motive power system 26 may include an engine (not shown), an energy source (such as gasoline, diesel fuel, or a one or more electric batteries in the case of a hybrid vehicle), and a transmission (not shown). The throttle system 29 may include elements and/or mechanisms (for example, an accelerator pedal), including computer-operable elements and/or mechanisms, configured to control the operating speed of the engine and, in turn, the speed of the vehicle 11.

Examples of specific autonomous and semi-autonomous systems and/or capabilities which may be incorporated into the vehicle 11 to facilitate autonomous vehicle control include adaptive cruise control, electronic stability control, automated lane centering, forward collision warning, lane departure warning, and blind spot monitoring. Additional controls, systems and/or capabilities may be provided if needed to perform the functions described herein, depending on the design of a particular vehicle. Vehicle embodiments described herein are assumed to include sufficient autonomous systems and/or capabilities to autonomously execute all of the commands needed to perform any of the vehicle maneuvers and operations needed to respond to a health alert generated by the health monitoring system by, for example, maneuvering the vehicle out of traffic to a safe location and stopping the vehicle.

Figure 7A:
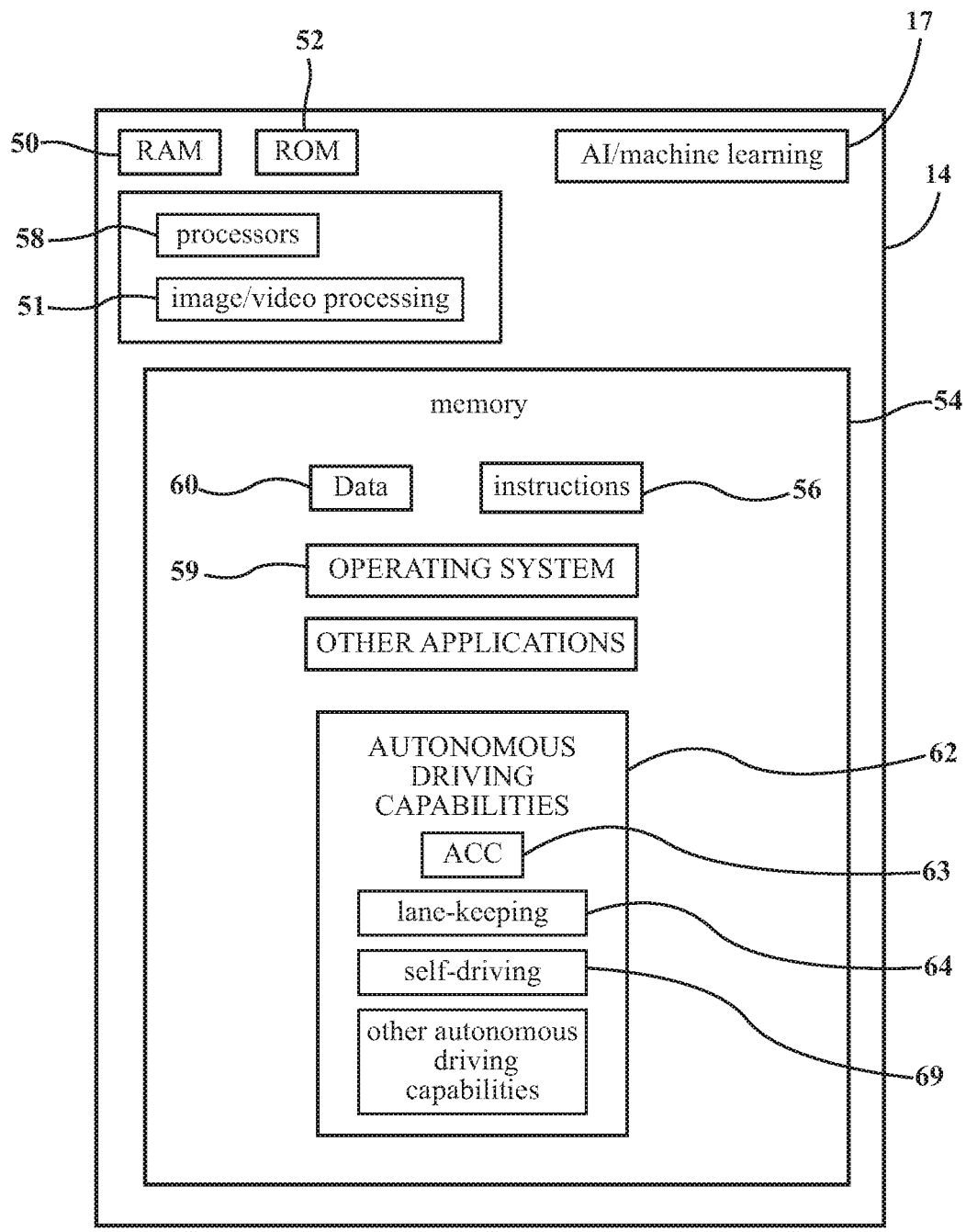
FIG. 7A is a schematic block diagram of a vehicle computing system according to one or more illustrative embodiments of the disclosure.

FIG. 7A is a block diagram of a vehicle computing system 14 that may be used according to one or more illustrative embodiments of the disclosure. The vehicle computing system 14 may be operatively connected to the other vehicle systems and elements and otherwise configured so as to implement partial or fully autonomous control and operation of the vehicle 11 and its components as described herein. The computing system 14 may control the functioning of the vehicle 11 based on inputs and/or information received from various subsystems (e.g., steering system 18, motive power system 26, etc.), from any of the vehicle communications interfaces 16, from sensor system 28, and/or from any other suitable source of information. The computing system 14 may have some or all of the elements shown in FIG. 7A. In addition, the computing system 14 may also include additional components as needed or desired for particular applications.

The computing system 14 may include one or more processors 58 for controlling overall operation of the computing system 14 and its associated components, including RAM 50, ROM 52, computer-readable storage or memory 54, and any other elements. Computing system 14 may execute instructions stored in a non-transitory computer readable medium, such as memory 54. In one or more arrangements, the processor(s) 58 can be a main processor of the vehicle 11. The computing system 14, along with any additional computing systems (e.g., any specialized primary sub-system controllers) (not shown) and other devices may correspond to any of multiple systems or devices configured as described herein for functions such as autonomously (i.e., without vehicle operator or occupant input) operating the entire vehicle or specific portions of the vehicle.

Computing system 14 may be configured to act as an autonomous vehicle controller, performing functions such as controlling (or assisting in coordinated control of) all autonomous driving operations, including steering, braking, etc. Computing system 14 may also be configured to operate (and/or coordinate operation of) the various vehicle systems and components so as to execute various autonomous commands or maneuvers, such as lane changes, merges, and turns, for example. Computing system 14 may also be configured to receive and store information from the vehicle sensor array 28 and/or from any other vehicle components pertaining to operation of the vehicle. The computing system 14 may also be configured to receive and store the information so that all of the information is time-correlated and may be processed for diagnostic or other purposes.

The vehicle computing system memory 54 may comprise one or more computer-readable memories. The memory 54 may contain data 60 and/or instructions 56 (e.g., program logic) executable by the processor(s) 58 to execute various functions of the vehicle 11. The memory 54 may contain additional instructions as well, including instructions to transmit data to, receive data from, interact with, or control one or more of the vehicle systems and/or components described herein (for example, motive power system 26, sensor system 28, computing system 14, and the vehicle communication interfaces 16). In addition to the instructions 56, the memory 54 may store data such as roadway maps, path information, among other information. Such information may be used by the vehicle 11 and the computer system 14 for route planning and otherwise during the operation of the vehicle 11 in autonomous, semi-autonomous, and/or manual modes.

The computing system 14 may be configured to coordinate control of the various actuatable vehicle systems and components so as to implement one or more autonomous driving capabilities (generally designated 62), including vehicle control capabilities such as a self-driving capability 69 and/or various autonomous driving assistance capabilities. A driving assistance capability may be defined as a capability which assists a driver in operating the vehicle by performing one or more functions which may be performed by the driver if the capability is absent or deactivated. The autonomous driving capabilities 62 may be stored in memory 54 and/or in other memories and implemented in the form of computer-readable program code that, when executed by a processor, implement one or more of the various processes, instructions or functions described herein. Any of the various capabilities described herein may be embodied in software, suitable hardware, and/or a combination of both hardware and software. Examples of driving assistance capabilities include adaptive cruise control (ACC) 63 and lane-keeping 64. A self-driving capability may be defined as an ability of the vehicle to perform all of the driving operations required to autonomously (i.e., without human input or interaction) drive the vehicle from a first or start location to a predetermined destination. The various autonomous driving assistance capabilities described herein may be part of the self-driving capability 69, or the various autonomous driving assistance capabilities described herein may be activated or utilized by the self-driving capability 69 to control the vehicle to drive the vehicle from a first or start location to the predetermined destination.

An adaptive cruise control capability (ACC) 63 may be defined as a cruise control system that automatically adjusts the vehicle speed to maintain a safe distance from vehicles ahead, based in information from onboard vehicle sensors. Thus, responsive to inputs from the vehicle sensors, for example, the computing system 14 may control the throttle system, braking system, motive power system and any other pertinent systems as required to implement the ACC functions. An autonomous lane keeping capability 64 may be defined as a system designed to monitor a relative position of the vehicle with respect to the boundaries of a traffic lane in which the vehicle is traveling, and to control the throttle system, steering system, any other pertinent systems as required to maintain the vehicle 11 in the current lane. The lane boundaries may be detected by vehicle sensors or by any other suitable method. In addition, elements of the autonomous lane keeping capability 64 and various sensors usable for the lane keeping function may be usable in detecting or determining a target lane into which a vehicle is to be autonomously steered pursuant to an autonomous lane change or traffic merging operation.

As stated previously, the computing system 14 may be configured to autonomously operate the vehicle 11 so as to drive the vehicle from a start location to a destination or end location located remotely from the start location, using self-driving capability 69. The computing system 14 may be configured to (responsive to inputs to the navigation system from vehicle sensors 28, such as cameras) operate the vehicle 11 in accordance with traffic lights and traffic signs along the planned route and to perform any other operations and functions necessary for self-driving the vehicle between the start and end locations. In one or more arrangements, the computing system 14 described herein can incorporate artificial or computational intelligence elements (e.g., neural network) or other machine learning algorithms, generally designated 17, to assist in the self-driving function. Further, in one or more arrangements, the hardware and/or software elements configured for performing particular functions or operations described herein may be distributed among a plurality of elements and/or locations. In addition to computing system 14, the vehicle may incorporate additional computing systems and/or devices (not shown) to augment or support the control functions performed by computing system 14, or for other purposes.

Information from sensors and other sources in the vehicle and exterior to the vehicle may be processed and used to control various vehicle systems and components. For example, various road condition sensors may be provided to supply information to the computing system 14 to enable the computing system to process the road condition information in accordance with stored processor-executable instructions, and to formulate appropriate control commands to the steering, throttle, and braking systems. The computing system 14 may continuously receive and process an ongoing or continuous flow of information from sensor system 28 and from other information sources. This information may be processed and/or evaluated in accordance with instructions stored in a memory, in a manner and for the purposes described herein.

Referring to FIGS. 7 and 7A, vehicle computing system 14 may operate (via vehicle communications interfaces 16) in a networked environment supporting connections to one or more remote computers, such as other computing systems, terminals and/or mobile devices (e.g., mobile phones, short-range vehicle communication systems, vehicle telematics devices, vehicle-to-vehicle communications systems, cloud computing systems, etc.). Any other computing systems or devices in the vehicle and any related terminals or devices in operative communication with vehicle computing system 14 may include devices installed in vehicles, mobile devices that may travel within vehicles, or devices outside of vehicles that are configured to receive and process vehicle and driving data. Thus, any terminals or devices in communication with the computing system 14 may each include personal computers (e.g., laptop, desktop, or tablet computers), servers (e.g., web servers, database servers, etc.), and other terminals or devices.

The vehicle communications interfaces 16 may include interfaces enabling communication in a wide area network (WAN), a wireless telecommunications network, and/or any other suitable communications networks (such as or including communications network 101, for example). The communication network(s) can include wired communication links and/or wireless communication links. The communication network(s) can include any combination of the above networks and/or other types of networks. The communication network(s) can include one or more routers, switches, access points, wireless access points, and/or the like. In one or more arrangements, the communication network(s) can include Vehicle-to-Everything (V2X) technologies (including Vehicle-to-Infrastructure (V2I) and Vehicle-to-Vehicle (V2V) technologies), which can allow for communications with any nearby vehicle(s), and between the vehicle 11 and any nearby roadside communications nodes and/or infrastructure.

When used in a WAN networking environment, the vehicle computing system 14 may include (or be operatively connected to) a modem or other means for establishing communications over the WAN, such as network (e.g., the Internet). When used in a wireless telecommunications network, the computing system 14 may include (or be operatively connected to) one or more transceivers, digital signal processors, and additional circuitry and software for communicating with wireless computing systems via one or more network devices (e.g., base transceiver stations) in the wireless network. These configurations provide various ways of receiving a constant flow of information from (and transmitting a constant flow of information to) various external sources. The communications interfaces 16 may be incorporated into the computing system 14 or may be located spaced apart from the computing system and communicatively coupled to the computing system.

An input/output module or human-machine interface (HMI) 109 may be provided to enable a user to communicate with the vehicle 11, with other vehicles, or with other entities. The user may provide input to (and receive output from) vehicle systems using the HMI 109. The HMI 109 may include an interactive display, a keyboard, a speech recognition interface and/or any other devices or capabilities needed to provide a desired level of interaction between the vehicle and the user.

Vehicle navigation module or system 23 may include, for example, a known navigation system receiver (for example, a GPS receiver) configured to receive vehicle location information from a GPS system or other source. However, vehicle navigation system 23 may have any alternative form or configuration suitable for the purposes described herein. Vehicle navigation system 23 may also be configured to operatively communicate with computing system 14 for providing vehicle navigational information for the purposes described herein. Computing system 14 may incorporate a suitable navigational system interface (not shown in FIG. 7A) if needed to facilitate operative communication with vehicle navigation system 23.

Vehicle navigation system 23 may include or be in operative communication with any sensor or sensors configured to estimate a geographic location of the vehicle 11. Vehicle navigation system 23 may perform (or assist in performing) any desired route planning for the vehicle, for example, using vehicle occupant destination inputs in a known manner. The vehicle navigation system 23 may be configured to determine or plan a driving route from a given start point (for example, a current location of the vehicle 11 or another designated start location) to a selected destination, using stored and/or available maps, in a manner known in the art. To these ends, the vehicle navigation system 23 may include a one or more transceivers, including a transceiver operable to provide information regarding the position and/or movement of the vehicle 11 with respect to Earth. Vehicle navigation system 23 may store data such as roadway maps and path information, among other information. Such information may be used by the computing system 14 (either alone or in conjunction with vehicle navigation system 23) in calculating and evaluating various routes that may be autonomously driven by the vehicle 11.

Referring again to FIG. 7, vehicle 11 may include an array 28 of vehicle sensors designed to monitor various vehicle operational status parameters and environmental conditions external to the vehicle. The vehicle sensor array 28 may include various types of sensors in communication with other vehicle components, for providing feedback on operations of the vehicle. For example, vehicle sensors 28 may detect and store data corresponding to the vehicle's location (e.g., GPS coordinates), speed and direction, rates of acceleration and/or braking, and specific instances of sudden acceleration, braking, and swerving. Vehicle sensors 28 also may detect and store data received from the vehicle's internal systems. Vehicle sensors 28 may detect and store information relating to external driving conditions, for example, external temperature, rain, snow, light levels, and sun position for driver visibility. For example, external cameras and proximity sensors, radar, lidar and other types of sensors may detect other nearby vehicles, traffic levels, road conditions, traffic obstructions, animals, cyclists, pedestrians, and other conditions that may factor into a driving condition analysis.

The sensors may be configured to detect and/or estimate various characteristics of other vehicles and other objects. For example, vehicle sensors 28 may be configured to detect whether a vehicle or other object is moving or stationary with respect to the surroundings. Vehicle sensors 28 may be configured to detect/and or estimate a direction and speed of a moving vehicle or object with respect to the vehicle 11 and with respect to other relatively static features (for example, trees or traffic signs) of the surroundings. Vehicle sensors 28 may be configured to detect whether or not another vehicle has a turn signal activated.

In a known manner, the vehicle sensors may provide data used by the vehicle computing system 14 in formulating and executing suitable control commands in the vehicle subsystems 18, 25, 26, 29, and also in other vehicle systems. For example, data from inertial sensors, wheel speed sensors, road condition sensors, and steering angle sensors may be processed in formulating and executing a command in steering system 18 to turn the vehicle. Vehicle sensors 28 may include any sensors required to support any driver assistance capabilities incorporated into the vehicle 11.

In arrangements in which the sensor system 28 includes a plurality of sensors, the sensors can work independently from each other. Alternatively, two or more of the sensors can work in combination with each other. Sensors of the sensor system 28 can be operatively connected to the computing system 14 and/or any other element of the vehicle 11. Non-exclusive examples of sensors that may be incorporated into a semi-autonomous or fully autonomous vehicle sensor array include radar and lidar systems, laser scanners, vision/camera systems, GPS systems, various inertial sensors such as an inertial measurement unit (IMU)

and/or gyroscopes and accelerometers, vehicle wheel speed sensors, road condition sensors, suspension height sensors, steering angle sensors, steering torque sensors, brake pressure sensors, accelerator or pedal position sensor, and tire pressure sensors.

The data collected by vehicle sensors 28 may be stored and/or analyzed within the vehicle and/or may be transmitted to one or more external devices. For example, the sensor data may be transmitted via telematics devices to one or more remote computing systems, such as a mobile device, or off-vehicle facility. Any data collected by vehicle sensors 28 may also be transmitted to any vehicle system or component requiring or utilizing the data for the purposes described herein. For example, the data collected by vehicle sensors 28 may be transmitted to computing system 14, or to one or more specialized system or component controllers (not shown).

Referring again to FIG. 7, if computing system 14 may require processing of an integrated or composite signal formed from outputs of multiple individual sensors, the vehicle 11 may incorporate a known sensor fusion means 138 (incorporating, for example, a suitable Kalman filter and/or another element incorporating or embodying a suitable sensor fusion algorithm) in communication with other pertinent vehicle systems, such as computing system 14, sensor system 28, and other vehicle systems. The sensor fusion means 138 may process data received from the various vehicle sensors to generate an integrated or composite signal formed, for example, from outputs of multiple individual sensors. The sensor fusion means 138 may further provide various assessments based on data from the sensor system 28. In an example embodiment, the assessments may include evaluations of individual objects or features in the environment of the vehicle 11, evaluation of a particular situation, and evaluation of possible impacts based on the particular situation. Other assessments are also possible. The sensor fusion means 138 may be stored on a memory (such as memory 54) or otherwise be in operative communication with computing system 14, and may be operated by the computing system in a manner known in the art.

Also, if a sensor output signal requires pre-processing prior to use by a controller or computing system 14, a known signal pre-processing means 38 (for example, an A/D converter) may be in communication with other pertinent vehicle systems, such as computing system 14, sensor system 28, and other vehicle systems. Similarly, if operation of any actuatable sub-system components or other vehicle components (for example, components of the steering system or throttle system) will require pre-processing of a control signal received from a controller, a known post-processing means 139 (for example, an D/A converter) may be provided in communication with other pertinent vehicle systems, such as computing system 14, sensor system 28, and other vehicle systems.

The vehicle 11 may be configured so that the various controllers, sensors and other elements of the system can communicate with each other using a controller area network (CAN) bus 33 (FIG. 7) or the like. Via the CAN bus and/or other wired or wireless mechanisms, the computing system 14 may transmit messages to various devices in the vehicle and/or receive messages from the various devices, e.g., controllers, actuators, sensors, etc. Alternatively, any of the elements and/or systems described herein may be directly connected to each other without the use of a bus. Also, connections between the elements and/or systems described herein may be through another physical medium (such as wired connections), or the connections may be wireless connections.

Referring now to FIGS. 7-10, in one or more arrangements, in an embodiment of the health monitoring system configured to monitor the pulse rate and motion of a driver or other occupant of a vehicle, the vehicle computing system 14 and an embodiment of the health monitoring system 19 may form, in combination, a vehicle control system configured for autonomously controlling the vehicle. The computing system memory 54 may store data and program instructions which are executable to control the vehicle responsive to receipt of the health alert signal from the health monitoring system.

The drawings illustrate embodiments of possible configurations of the health monitoring system when operating in a vehicle environment. FIG. 8 is a schematic diagram showing in more detail the application of a distributed configuration of the health monitoring system shown in FIG. 7. In the embodiment shown in FIGS. 7 and 8, for example, the health monitoring system processors 22, memory 24, and an associated communications interface 27 are located in a cloud (or other remote) computing environment 91, while the health monitoring system sensors 20a, 20b and an associated communications interface 20d are positioned in the vehicle in the health monitoring system sensor unit 20. Communications interface 27 may be communicatively coupled to the processors 22 and the memory 24, and may enable wireless communication between the processors 22/memory 24 and other elements, systems and/or entities external to the cloud computing environment 91 (including health monitoring system sensors 20a, 20b). For example, health monitoring system communications interface 27 may be configured to enable communication between the health monitoring system 19 and entities such as emergency services 97, various mobile or cellular devices 98, and/or the vehicle 11 in which the user resides.

Sensors 20a, 20b (either separately or incorporated into sensor unit 20) are operatively attached to a user (not shown). Communications interface 20d (FIG. 1) is communicatively coupled to the sensors 20a, 20b and may enable wireless communication between sensors 20a, 20b and processors 22/memory 24. Although the sensors 20a, 20b and communications interface 20d in the embodiment of FIGS. 7 and 8 are shown and described as being positioned in a vehicle 11 for measuring pulse rate and activity level of a user in the form of a vehicle occupant, the sensors 20a, 20b and communications interface 20d may, in one or more other arrangements, be applied to a user who is not in a vehicle 11 and has no connection to a vehicle 11.

Also, vehicle communications interfaces 16 may be configured to establish and enable continued and uninterrupted interaction between the vehicle 11 and external sensors, other vehicles 94 (via V2V communications network 93), emergency services 97, cellular phone/mobile devices 98, other computer systems (such as a cloud computing environment 91) and/or other remote external computing and communications systems and networks (such as communications network 101), including off-vehicle computing facilities incorporating one or more of the capabilities described herein, and useable for performing one or more of the functions described herein. The health monitoring system 19 may communicate wirelessly or by a wired connection with the vehicle computing system 14 (via vehicle communications interfaces 16) so that the vehicle computing system 14 may operate the vehicle responsive to receipt of a health alert.

In one or more arrangements, the vehicle communications interfaces 16 may be configured to communicate (via wire or wirelessly) with the health monitoring system sensors 20*a*, 20*b*. The sensors 20*a*, 20*b* may then communicate wirelessly with a remote computing environment or other entity using the vehicle communications interfaces 16.

Figure 9:
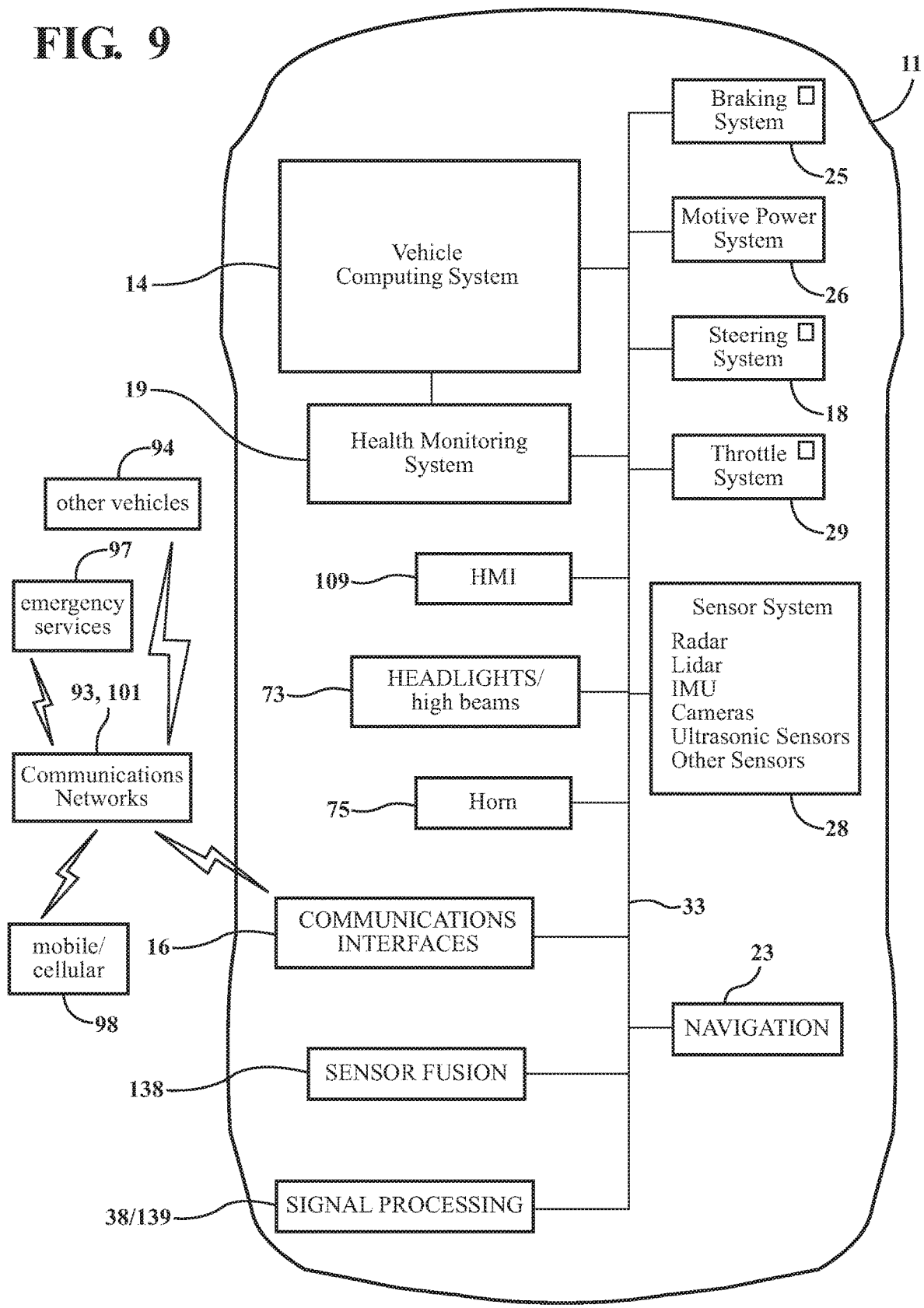
FIG. 9 is a block schematic diagram of a health monitoring system/vehicle configuration in accordance with another embodiment described herein.

FIG. 9 is a block schematic diagram of another embodiment of a health monitoring system/vehicle configuration. This embodiment may be configured the same as the embodiment shown in FIG. 7, except where noted herein. In this configuration, the entire health monitoring system 19 is located in the vehicle 11. The health monitoring system 19 may be configured for wired or wireless communication with the vehicle computing system 14 and/or other elements of the vehicle. In this embodiment, signals to other entities (such as other vehicles 94) may be transmitted using one of the health monitoring system communications interfaces previously described or the vehicle communications interfaces 16. When the health monitoring system 19 is configured for communications using the vehicle communications interfaces 16, the health monitoring system communications interface to the external environment may be eliminated. In one or more arrangements, the elements of the health monitoring system 19 may be configured to form a self-contained, man-portable unit which may be carried by an individual user and used in any one of multiple vehicles. Other than as noted, the health monitoring system/vehicle configuration shown in FIG. 9 may operate as previously described.

Figure 10:
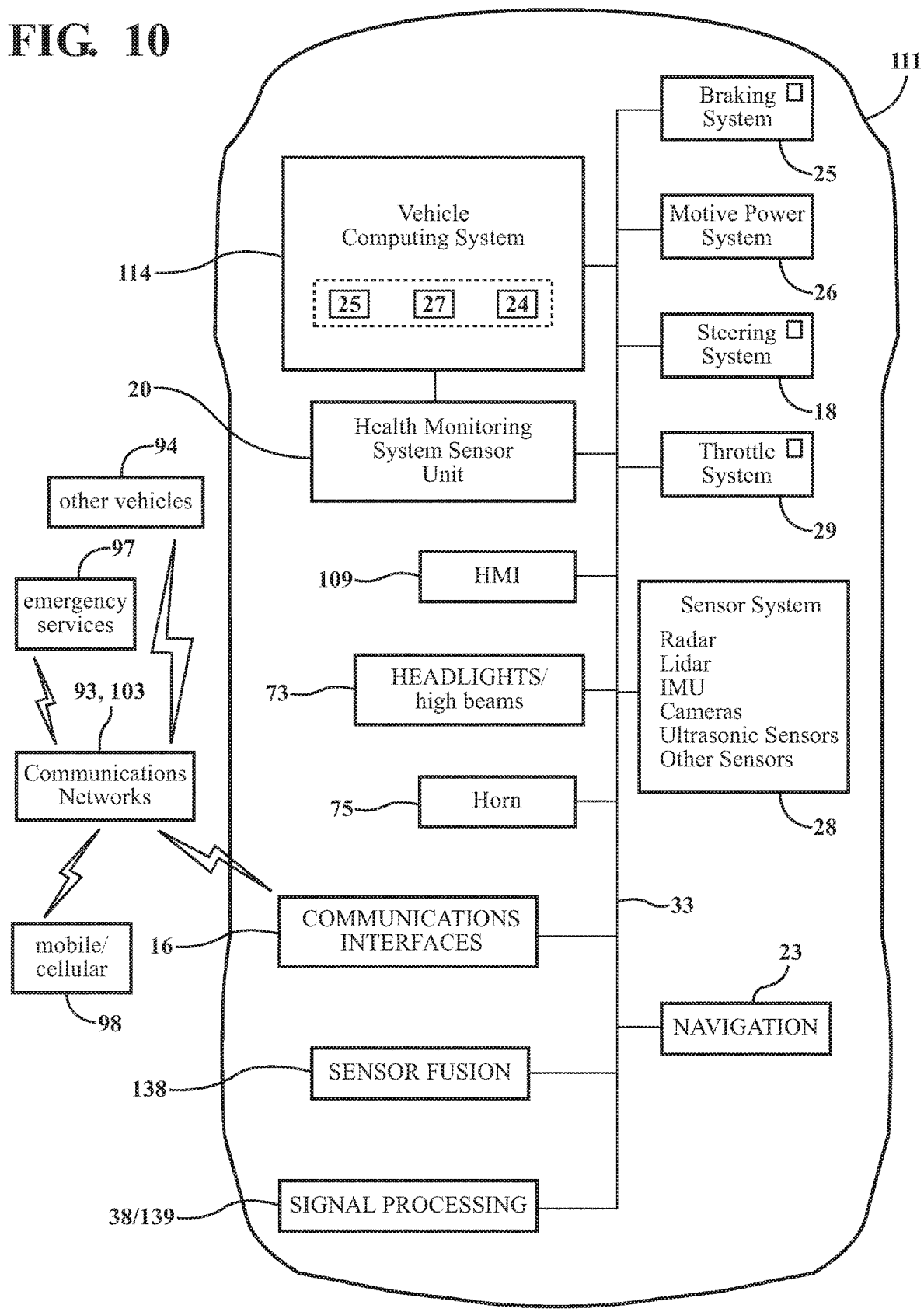
FIG. 10 is a block schematic diagram of a health monitoring system/vehicle configuration in accordance with yet another embodiment described herein.

FIG. 10 is a block schematic diagram of yet another embodiment of a health monitoring system/vehicle configuration. This embodiment may be configured the same as the embodiment shown in FIG. 9, except where noted herein. In this configuration, the entire health monitoring system 19 is located in the vehicle 211. In the embodiment shown in FIG. 10, the health monitoring system processors 22 and memory 24 may be incorporated into the vehicle computing system 114, and may be in communication with other portions of the computing system. The computing system 114 may otherwise be configured as described previously with respect to FIG. 7A.

A health monitoring system communications interface 27 may also be provided for enabling communications between the processors 22 and memory 24 and health monitoring system sensors 20*a*, 20*b*. Sensors 20*a*, 20*b* may be configured for wireless communication with the processors 22 and memory 24 in a manner previously described. Sensors 20*a*, 20*b* may also be configured for wired communication with the processors 22 and memory 24, for example, by plugging the sensors directly into ports provided in the vehicle. Other than as noted, the health monitoring system/vehicle configuration shown in FIG. 10 may operate as previously described.

As will be appreciated by one skilled in the pertinent art upon reading the preceding disclosure, various aspects described herein may be embodied as a method, a computer system, or a computer program product. Accordingly, those aspects may take the form of an entirely hardware embodiment, an entirely software embodiment or an embodiment combining software and hardware aspects. Furthermore, such aspects may take the form of a computer program product stored by one or more computer-readable storage media having computer-readable program code, or instructions, embodied in or on the storage media for executing the functions described herein. Any suitable computer readable storage media may be utilized, including hard disks, CD-ROMs, optical storage devices, magnetic storage devices, and/or any combination thereof. In addition, various signals representing data or events as described herein may be transferred between a source and a destination in the form of electromagnetic waves traveling through signal-conducting media such as metal wires, optical fibers, and/or wireless transmission media (e.g., air and/or space).

It should be understood that the preceding is merely a detailed description of various embodiments of this invention and that numerous changes to the disclosed embodiments can be made in accordance with the disclosure herein without departing from the spirit or scope of the invention. Thus, the disclosure is not to be limited to these embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method of controlling a vehicle, comprising steps of:
   acquiring occupant pulse rate information and occupant motion information for an occupant of the vehicle;
   classifying, using the occupant motion information, a current activity level of the occupant into one of a plurality of predetermined activity levels;
   determining a range of safe pulse rates for the occupant at the current activity level, the step of determining the range of safe pulse rates including determining a safe minimum pulse rate for the occupant at the current activity level of the occupant and determining a safe maximum pulse rate for the occupant at the current activity level of the occupant;
   determining, using the range of safe pulse rates for the occupant, if a current pulse rate of the occupant indicates a cardiac health risk to the occupant; and
   responsive to a determination that the current pulse rate of the occupant indicates a cardiac health risk to the occupant, controlling the vehicle.

2. The method of claim 1 wherein the occupant motion information comprises x, y, and z components of an acceleration of a portion of a body of the occupant during movement of the portion of the body at the current activity level of the occupant.

3. The method of claim 1 wherein the step of determining if the current pulse rate of the occupant indicates a cardiac health risk to the occupant comprises steps of:
   determining when the current pulse rate of the occupant is outside the range of safe pulse rates;
   responsive to a determination that the current pulse rate of the occupant is outside the range of safe pulse rates, determining if a difference between the current pulse rate of the occupant and a second most recent pulse rate exceeds a predetermined threshold value;
   responsive to a determination that the difference between the current pulse rate of the occupant and the second most recent pulse rate exceeds the predetermined threshold value, determining if a difference between the second most recent pulse rate and a third most recent pulse rate exceeds the predetermined threshold value; and
   responsive to a determination that the difference between the second most recent pulse rate and the third most recent pulse rate exceeds the predetermined threshold value, determining that the current pulse rate of the occupant indicates a cardiac health risk to the occupant.

4. The method of claim 3 wherein the step of determining when the current pulse rate of the occupant is outside the range of safe pulse rates comprises steps of:
- determining if the current pulse rate of the occupant is below the safe minimum pulse rate for the occupant at the current activity level of the occupant; and
- determining if the current pulse rate of the occupant is above the safe maximum pulse rate for the occupant at the current activity level of the occupant.

5. The method of claim 3 further comprising the step of, responsive to a determination that the current pulse rate of the occupant is not outside the range of safe pulse rates, storing occupant pulse rate information and occupant motion information in a memory, wherein the occupant pulse rate information and occupant motion information are time-correlated.

6. The method of claim 3 further comprising the step of, responsive to a determination that the difference between the current pulse rate of the occupant and the second most recent pulse rate does not exceed the predetermined threshold value, storing the current pulse rate of the occupant that is outside the range of safe pulse rates in a memory.

7. The method of claim 3 further comprising step of, responsive to a determination that the difference between the second most recent pulse rate and the third most recent pulse rate does not exceed the predetermined threshold value, storing the current pulse rate of the occupant that is outside the range of safe pulse rates in a memory.

8. The method of claim 1 further comprising the steps of:
- acquiring environmental information;
- time-correlating the environmental information with the occupant pulse rate information and the occupant motion information; and
- storing the time-correlated environmental information in a memory.

9. The method of claim 1 further comprising the step of, responsive to a determination that the current pulse rate of the occupant indicates a cardiac health risk to the occupant, generating one or more alerts directed to at least one of emergency medical personnel and any vehicles residing within a predetermined distance of the vehicle.

10. A system for autonomously controlling a vehicle, the system comprising:
- a vehicle computing system; and
- a health monitoring system including one or more health monitoring system processors, and a health monitoring system memory in communication with the one or more health monitoring system processors, the health monitoring system memory being configured for storing information and program instructions usable by the one or more health monitoring system processors, and wherein the health monitoring system memory stores,
- a user activity level classification module including instructions that when executed by the one or more health monitoring system processors cause the one or more processors to classify a current activity level of a vehicle occupant using motion information relating to the vehicle occupant;
- a cardiac health risk determination module including instructions that when executed by the one or more health monitoring system processors cause the one or more processors to determine if a current pulse rate of the vehicle occupant at the current activity level indicates a cardiac health risk to the vehicle occupant; and
- a health alert generation module including instructions that when executed by the one or more processors cause the one or more processors to, responsive to a determination that a current pulse rate of the vehicle occupant indicates a cardiac health risk to the vehicle occupant, generate one or more health alert signals to the vehicle computing system,
- the vehicle computing system being in communication with the health monitoring system and configured for autonomously controlling the vehicle, the vehicle computing system including one or more processors for controlling operation of the vehicle computing system, and a memory for storing data and program instructions usable by the one or more processors for controlling operation of the vehicle computing system, wherein the one or more processors for controlling operation of the vehicle computing system are configured to execute instructions stored in the memory to control the vehicle responsive to receipt of a health alert signal from the health monitoring system.

11. The system of claim 10 wherein the cardiac health risk determination module further includes instructions that when executed by the one or more health monitoring system processors cause the one or more processors to determine a range of safe pulse rates for the vehicle occupant at the current activity level of the occupant, and to determine, using the range of safe pulse rates for the vehicle occupant, if a current pulse rate of the occupant at the current activity level indicates a cardiac health risk to the vehicle occupant.

12. The system of claim 11 wherein the cardiac health risk determination module further includes instructions that when executed by the one or more processors cause the one or more processors to:
- determine when a current pulse rate of the vehicle occupant is outside the range of safe pulse rates;
- responsive to a determination that the current pulse rate of the vehicle occupant is outside the range of safe pulse rates, determine if a difference between the current pulse rate of the vehicle occupant and a second most recent pulse rate exceeds a predetermined threshold value;
- responsive to a determination that the difference between the current pulse rate of the vehicle occupant and a second most recent pulse rate exceeds the predetermined threshold value, determine if a difference between the second most recent pulse rate and a third most recent pulse rate exceeds the predetermined threshold value; and
- responsive to a determination that the difference between the second most recent pulse rate and the third most recent pulse rate exceeds the predetermined threshold value, determine that the current pulse rate of the vehicle occupant at the current activity level indicates a cardiac health risk to the vehicle occupant.

13. The system of claim 10 wherein the health monitoring system further comprises a pulse rate sensor configured to provide occupant pulse rate information to the one or more health monitoring system processors, and at least one motion sensor configured to provide vehicle occupant motion information to the one or more health monitoring system processors.

14. The system of claim 13 wherein the pulse rate sensor and the at least one motion sensor are incorporated into a sensor unit configured to be wearable by a vehicle occupant.

15. The system of claim 10 further comprising at least one communications interface configured to enable communication of vehicle occupant pulse rate information and vehicle occupant motion information to the one or more health monitoring system processors and/or the health monitoring system memory.

16. The system of claim 15 wherein the one or more health monitoring system processors and the health monitoring system memory are configured to be positionable in the vehicle or are incorporated into a cloud computing network physically separated from the vehicle.

17. The system of claim 10 further comprising at least one communications interface configured to enable communication between the health monitoring system and the vehicle computing system.

18. The system of claim 10 further comprising at least one communications interface configured to enable communication between the health monitoring system and vehicles other than the vehicle.

19. The system of claim 10 wherein the one or more processors for controlling operation of the vehicle computing system are configured to execute instructions stored in the memory to generate one or more alerts directed to emergency medical personnel and/or any vehicles residing within a predetermined distance of the vehicle.

* * * * *